(12) United States Patent
Duan

(10) Patent No.: US 11,700,437 B2
(45) Date of Patent: Jul. 11, 2023

(54) CAPSULE ENDOSCOPE WITH A DYNAMIC ADJUSTABLE COLOR ILLUMINATION SPECTRUM

(71) Applicant: AnX Robotica Corp., Plano, TX (US)

(72) Inventor: Xiaodong Duan, Pleasanton, CA (US)

(73) Assignee: AnX Robotica Corp., Plano, TX (US)

( * ) Notice: Subject to any disclaimer, the term of this patent is extended or adjusted under 35 U.S.C. 154(b) by 0 days.

(21) Appl. No.: 17/124,277

(22) Filed: Dec. 16, 2020

(65) Prior Publication Data
US 2022/0191438 A1 Jun. 16, 2022

(51) Int. Cl.
| | | |
|---|---|---|
| *H04N 5/76* | (2006.01) | |
| *H04N 23/10* | (2023.01) | |
| *G06T 7/50* | (2017.01) | |
| *H04N 23/51* | (2023.01) | |
| *H04N 23/54* | (2023.01) | |
| *H04N 23/56* | (2023.01) | |
| *H04N 23/50* | (2023.01) | |

(52) U.S. Cl.
CPC ............ *H04N 23/125* (2023.01); *G06T 7/50* (2017.01); *H04N 5/76* (2013.01); *H04N 23/51* (2023.01); *H04N 23/54* (2023.01); *H04N 23/56* (2023.01); *G06T 2207/10068* (2013.01); *G06T 2207/30004* (2013.01); *H04N 23/555* (2023.01)

(58) Field of Classification Search
None
See application file for complete search history.

(56) References Cited

U.S. PATENT DOCUMENTS

| | | |
|---|---|---|
| 7,009,634 B2 | 3/2006 | Iddan et al. |
| 7,116,352 B2 | 10/2006 | Yaron |
| 8,681,209 B2 | 3/2014 | Iddan et al. |
| 9,986,898 B2 | 6/2018 | Duan et al. |
| 9,999,415 B2 | 6/2018 | Duan et al. |
| 10,076,234 B2 | 9/2018 | Duan et al. |
| 10,314,514 B2 | 6/2019 | Duan |
| 10,478,047 B2 | 11/2019 | Duan et al. |
| 10,500,127 B2 | 12/2019 | Duan et al. |

(Continued)

OTHER PUBLICATIONS

International Search Report for PCT Appl. No. PCT/US2021/062796 dated Mar. 1, 2022.

*Primary Examiner* — Eileen M Adams
(74) *Attorney, Agent, or Firm* — Pearl Cohen Zedek Latzer Baratz LLP

(57) ABSTRACT

A capsule endoscope device, system and method for dynamically adjusting a color illumination spectrum. A plurality of different color groups of LEDs may emit light, recorded by an image sensor, corresponding to a plurality of different respective wavelength subranges. A driving circuit may send a driving current to independently activate each different color group of LEDs during entirely or partially non-overlapping time pulses. A single color group of LEDs is independently activated at any one time, and the plurality of different color groups of LEDs are sequentially activated in successive time pulses to simulate a white light or multi-color illumination spectrum over a plurality of the time pulses. The activation pattern of the color groups of LEDs may be dynamically adjusted, in real-time, to achieve a flexible and customizable illumination spectrum ideal for imaging a variety of different environments e.g., in the GI tract.

17 Claims, 20 Drawing Sheets

(56) References Cited

U.S. PATENT DOCUMENTS

| | | |
|---|---|---|
| 10,517,466 B2 | 12/2019 | Ye et al. |
| 2003/0030756 A1* | 2/2003 | Kane ................ H04N 9/3132 |
| | | 348/196 |
| 2003/0117491 A1 | 6/2003 | Avni et al. |
| 2003/0124466 A1* | 7/2003 | Goodin ................ B41C 1/055 |
| | | 118/620 |
| 2011/0089010 A1 | 4/2011 | Hsu et al. |
| 2011/0213203 A1* | 9/2011 | Minai ................ A61B 1/0655 |
| | | 600/109 |
| 2013/0267788 A1 | 10/2013 | Duan et al. |
| 2014/0187907 A1 | 7/2014 | Duan et al. |
| 2014/0247039 A1 | 9/2014 | Duan et al. |
| 2015/0011829 A1 | 1/2015 | Wang et al. |
| 2015/0380140 A1 | 12/2015 | Duan et al. |
| 2016/0310357 A1 | 10/2016 | Duan et al. |
| 2017/0020374 A1 | 1/2017 | Duan et al. |
| 2017/0035520 A1 | 2/2017 | Duan et al. |
| 2017/0296428 A1 | 10/2017 | Duan et al. |
| 2018/0084976 A1 | 3/2018 | Duan et al. |
| 2020/0217716 A1* | 7/2020 | Imoto ...................... G01J 1/04 |
| 2021/0161373 A1* | 6/2021 | Tearney .................. A61B 1/07 |

* cited by examiner

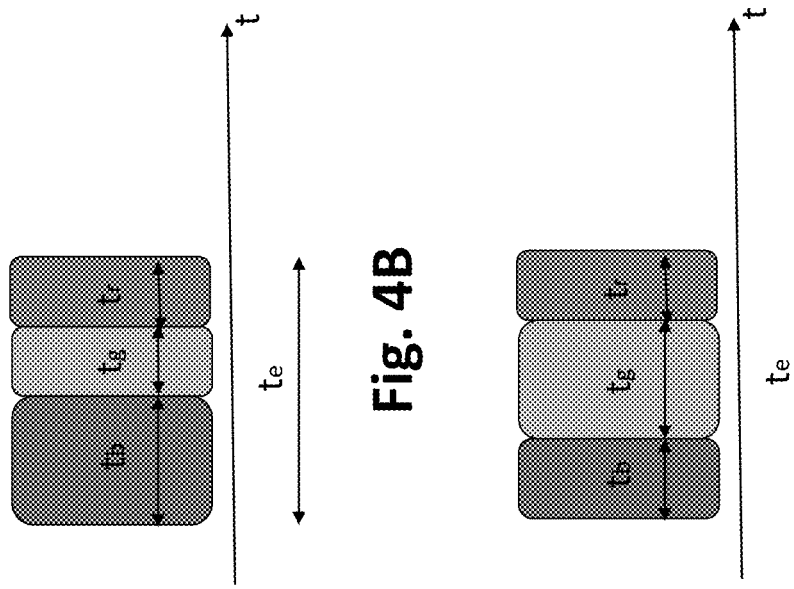
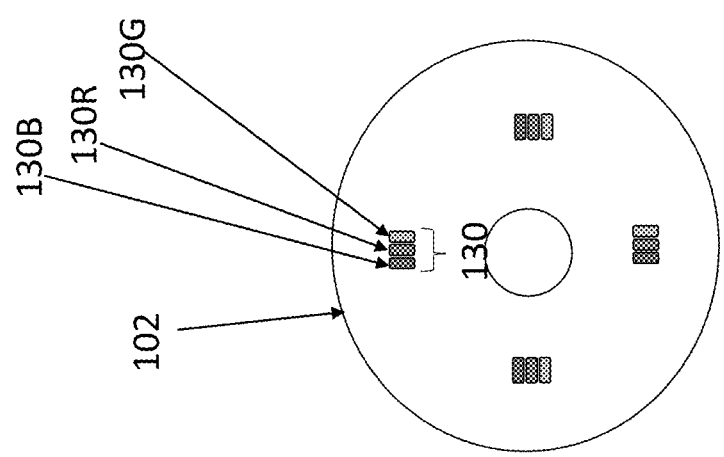

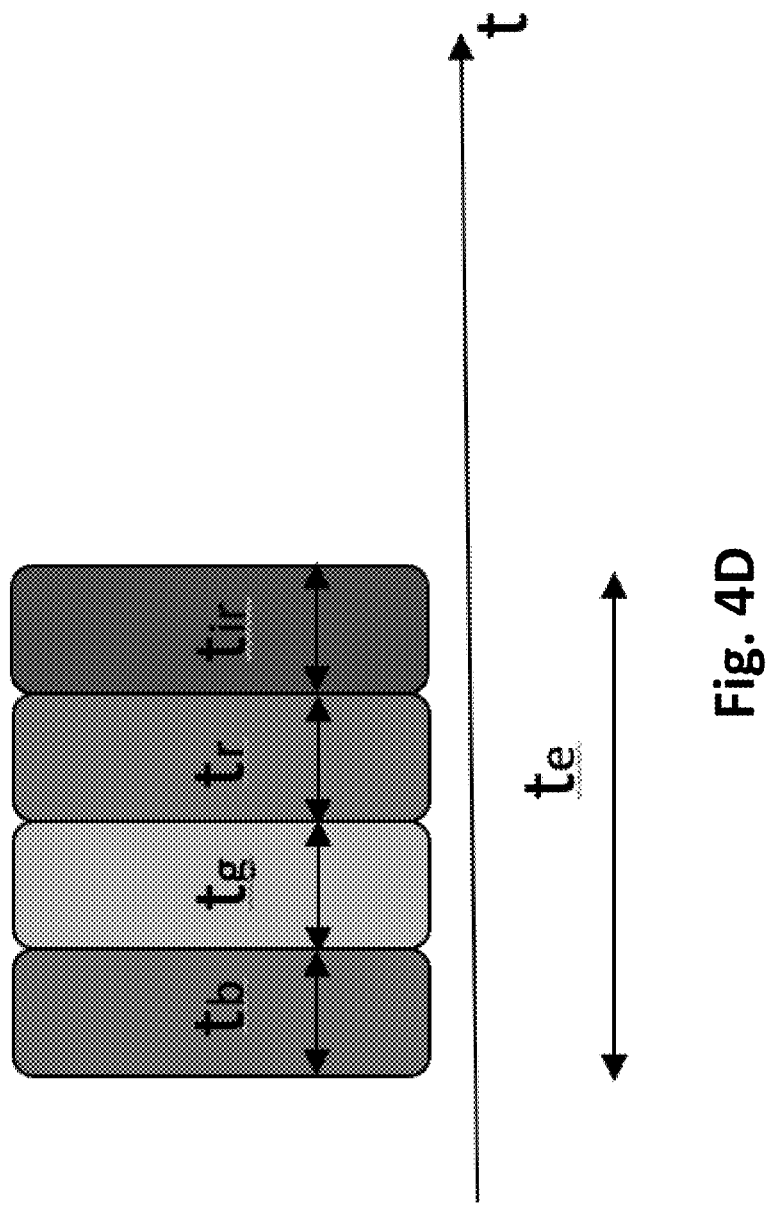

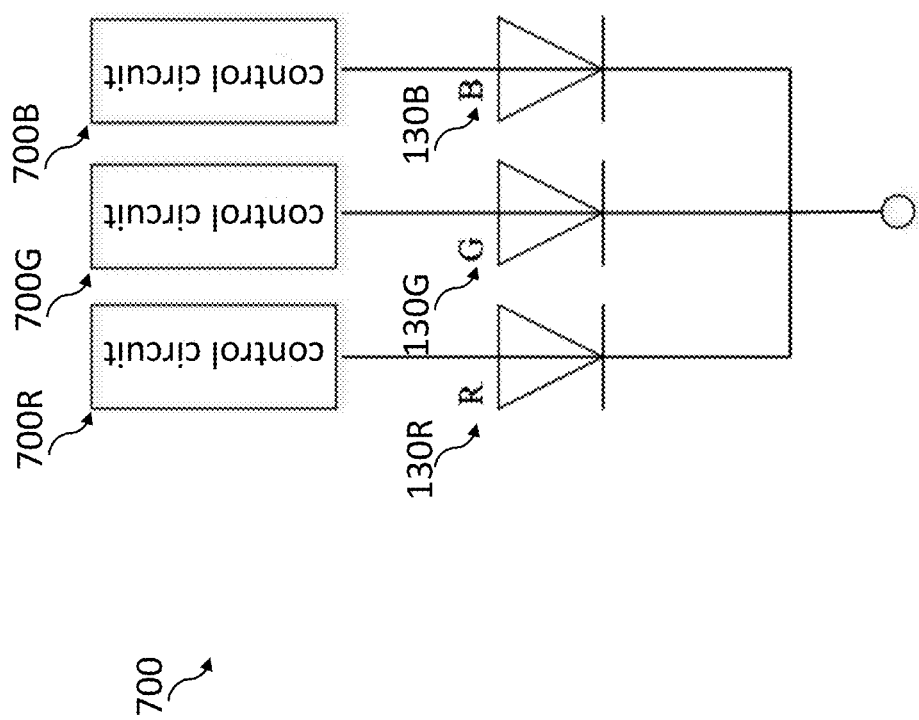

| # | Wavelength (nm) | FWHM (nm) | 2θ (°) |
|---|---|---|---|
| Blue1 | 400 | 12 | 120 |
| Blue2 | 415 | 16 | 120 |
| Blue3 | 460 | 22 | 120 |
| Green1 | 515 | 34 | 120 |
| Green2 | 577 | 15 | 120 |
| Red1 | 591 | 14 | 120 |
| Red2 | 611 | 14 | 120 |
| Red3 | 631 | 18 | 120 |

Fig. 8

CAPSULE ENDOSCOPE WITH A DYNAMIC ADJUSTABLE COLOR ILLUMINATION SPECTRUM

FIELD OF THE INVENTION

Embodiments of the invention relate to an ingestible or in-vivo capsule endoscopic imaging device and system such as for imaging the gastro-intestinal (GI) tract.

BACKGROUND OF THE INVENTION

Conventional capsule endoscopes use light emitting diodes (LEDs) as illumination sources. Conventional LEDs have a fixed or non-adjustable wavelength or illumination spectrum. A typical illumination spectrum of white light LEDs combines red, green, and blue LEDs in equal proportion (a 1:1:1 ratio). These LEDs illuminate the GI track with a constant spectrum of colors that does not change.

However, the GI tract is a diverse network of organs, channels, and cavities. Different anatomical regions have different optimal absorption spectra and therefore different corresponding optimal illumination spectra. For example, areas with dense networks of superficial blood vessels (e.g., near the tracheobronchial tree and the colorectal region) have maximal absorption peaks when illuminated at wavelengths near 415 nm (blue light) and 540 nm (green light). In contrast, white light illumination spectrum is best for imaging subepithelial lesions (SELs) commonly found in the stomach. Conventional LEDs use the same fixed illumination profile as the capsule endoscope travels through all areas of the GI tract. While a fixed illumination profile may be optimal for some regions, the same illumination profile is generally suboptimal for other regions.

Accordingly, there is a long felt need in the art for an illumination source that provides optimal illumination spectra across the various diverse areas of the GI tract.

SUMMARY OF EMBODIMENTS OF THE INVENTION

Embodiments of the invention solve this long felt need in the art by providing an adaptive illumination source that provides different illumination spectra independently determined to be optimal for different respective areas of the GI tract. Adaptive illumination may be achieved by independently activating different color groups of LEDs in sequential time pulses, so that at any one time, only a single color group (and no other color group at that same or overlapping time) is illuminated, but cumulatively multiple color groups combine to form white light and/or multi-color (non-white) light spectra over multiple time pulses to illuminate an image. Adaptive illumination sources provide the flexibility to customize the illumination profile to be ideal for imaging a variety of different environments.

In an embodiment of the invention, a capsule endoscope device, system and method is provided for dynamically adjusting a color illumination spectrum. A capsule-shaped body may have at least one transparent optical end, the capsule-shaped body enclosing electronic components therein. An image sensor, to record in-vivo images, housed interior to the capsule-shaped body behind the at least one transparent optical end. A plurality of different color groups of LEDs may emit light to be recorded by the image sensor, the plurality of different color groups of LEDs corresponding to a plurality of different respective wavelength subranges. A driving circuit may send a driving current to independently activate each different color group of LEDs during different (e.g., entirely or partially non-overlapping) time pulses, such that, a single color group of LEDs may be independently activated at any one time, and the plurality of different color groups of LEDs are sequentially activated in successive time pulses to simulate a white light or multi-color illumination spectrum over a plurality of time pulses.

In an embodiment of the invention, a capsule endoscope device, system and method is provided for emitting a dynamic adjustable color illumination spectrum. A plurality of different color groups of LEDs may be sequentially activated during entirely or partially non-overlapping time pulses, wherein the plurality of different color groups of LEDs illuminate biological tissue with light in a plurality of different respective wavelength subranges. A plurality of different color groups of images may be sequentially stored and recorded, at an image sensor, depicting the scattering of light emitted from the respective plurality of color groups of LEDs during the entirely or partially non-overlapping time pulses. Images from two or more of the plurality of different color groups of images may be combined to form white light or non-white multi-color images.

In an embodiment of the invention, a capsule endoscope device, system and method is provided for emitting a dynamic adjustable color illumination spectrum. A plurality of different color groups of light emitting diodes (LEDs) may be sequentially activated during entirely or partially non-overlapping time pulses, wherein the plurality of different color groups of LEDs illuminate biological tissue with light in a plurality of different respective wavelength subranges. White light or non-white multi-color images may be recorded, at an image sensor. Each white light or non-white multi-color image that is stored may depict the scattering of light cumulatively emitted from two or more of the plurality of color groups of LEDs during a combination of two or more of the associated entirely or partially non-overlapping time pulses.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4A is a close-up view of an LED array of FIG. 1A, according to some embodiments of the invention;

FIG. 4B-4D are graphs of a plurality of patterns of time pulses during which a plurality of different color groups of LEDs are independently activated, according to some embodiments of the invention;

FIG. 7C is a schematic illustration of a driving circuit comprising a plurality of dedicated control circuits, each of which independently activates a different respective color group of LEDs, according to some embodiments of the invention;

FIG. 8 is a table listing a plurality of different respective color groups of LEDs and their corresponding peak wavelengths, full width half maximums, and beam angles, according to some embodiments of the invention.

Figure 1A:
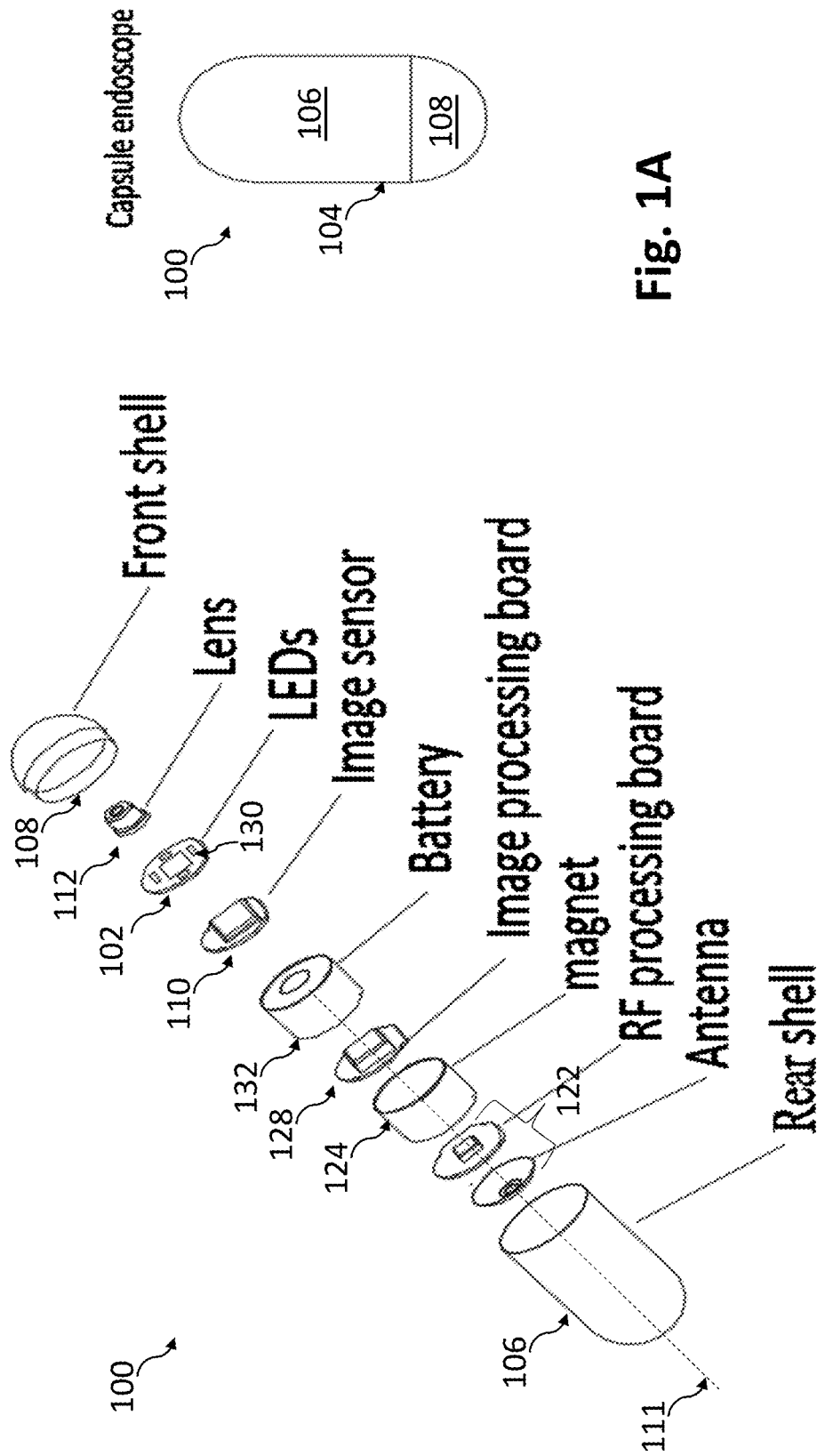
FIG. 1A is a schematic illustration of an exploded view of an in-vivo capsule endoscope with a dynamic adjustable color illumination spectrum and components thereof, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

Color is a property of an electromagnetic wave that characterizes its wavelength(s) in visible light or non-visible (e.g., IR) light ranges. This wavelength range may be divided into subranges or groups called "color groups," such as a red, blue, green group (in the visible range) or IR color group (in the non-visible range).

Figure 5A:
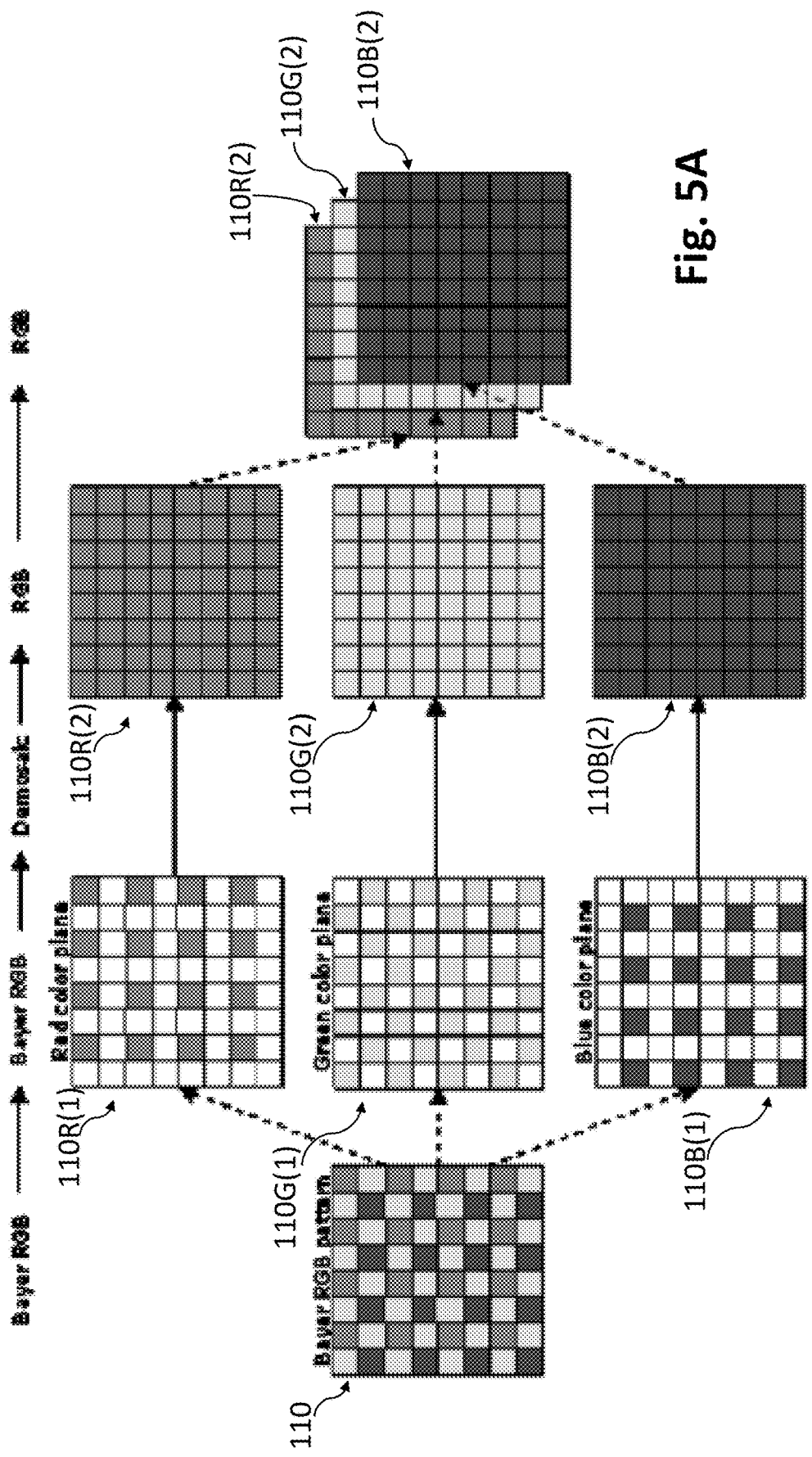
FIG. 5A is a schematic illustration of an image sensor with an example color pattern created by a color filter array, such as a Bayer filter, according to some embodiments of the invention.

A capsule endoscope according to embodiments of the invention (e.g., as shown in FIG. 1A) has illumination sources with a dynamically adjustable illumination spectrum. The illumination spectrum is adjusted by independently and sequentially activating each set of LEDs in the same color group (e.g., red, green, or blue LEDs and/or IR LEDs) in a plurality of successive time pulses (e.g., red time pulse, green time pulse, and/or blue time pulse, as shown in the time pulse patterns of FIGS. 4B-4D). At any one time, only a single color group of LEDs (e.g., red, green, blue or IR LEDs) is activated and no other color groups are activated at that same or overlapping times. However, over multiple activation periods, these color groups combine to cumulatively form a combination of color groups, which may be referred to as white light or multi-color (non-white) light. The activation duration or "pulse width" of each color group of LEDs is the amount of time those LEDs are activated and emit light. An image sensor (e.g., as shown in FIG. 5A) may record light during the activation of each individual color group separately to generate an archived set of a plurality of color-independent images (e.g., a red image, a blue image and a green image) and/or a mixed-color image (e.g., a white light image). A driving circuit (e.g., as shown in FIG. 7C) may dynamically adjust the combination or order of activated color groups of LEDs, the time pulse widths (e.g., to adjust the activation duration) of each activated color group of LEDs, and/or the driving currents (e.g., to adjust the illumination intensity and/or relative radiation power) of each activated color group of LEDs, to effect different color combinations for multiple images. The combination of those LED color groups may be mixed in adjustable proportions to optimize the illumination spectrum for the surrounding environment being imaged in the GI tract. Due to the dynamic and flexible nature of this illumination spectrum, embodiments of the invention can create optimal illumination profiles for a variety of different anatomical regions to improve the accuracy of images across the GI tract.

In some embodiments, the dynamic illumination spectrum of the LEDs may be adjusted based on a real-time feedback loop. The feedback loop may be based on visual information from the captured images (e.g., on an image by image basis) or based on real-time position information defining the exact or approximate location or anatomical region in which the capsule is located. The feedback loop inputs captured environmental information (e.g., visual or position information), calculates or retrieves new optimal illumination spectra parameters associated with that environmental information, and outputs those new parameters to reset the LED activation time pulses or driving currents. For example, images that are too red may trigger a driving circuit to shorten the red-LED time pulse. In another example, position feedback information may indicate the capsule has passed into the stomach, or is within a specific distance from a lumen or wall, causing a corresponding lighting adjustment. These embodiments will dynamically adjust the illumination patterns in real-time to instantaneously (or near instantaneously) improve imaging of different anatomical regions of the GI tract.

Adaptation may occur during real-time recording by adjusting the LEDs (e.g., adjusting activation patterns, durations and/or driving currents of LEDs) and/or during post-processing by adjusting the archived images (e.g., combining various ratios of color-images). For example, adjusting the LEDs may involve activating a red LED with a pulse length N times as long as the blue LED pulse length (e.g., adjusting LED illumination times). An equivalent effect may be performed using archived images by combining N times more red color images than blue color images (e.g., adjusting the weight of various color image combinations).

Figure 3A:
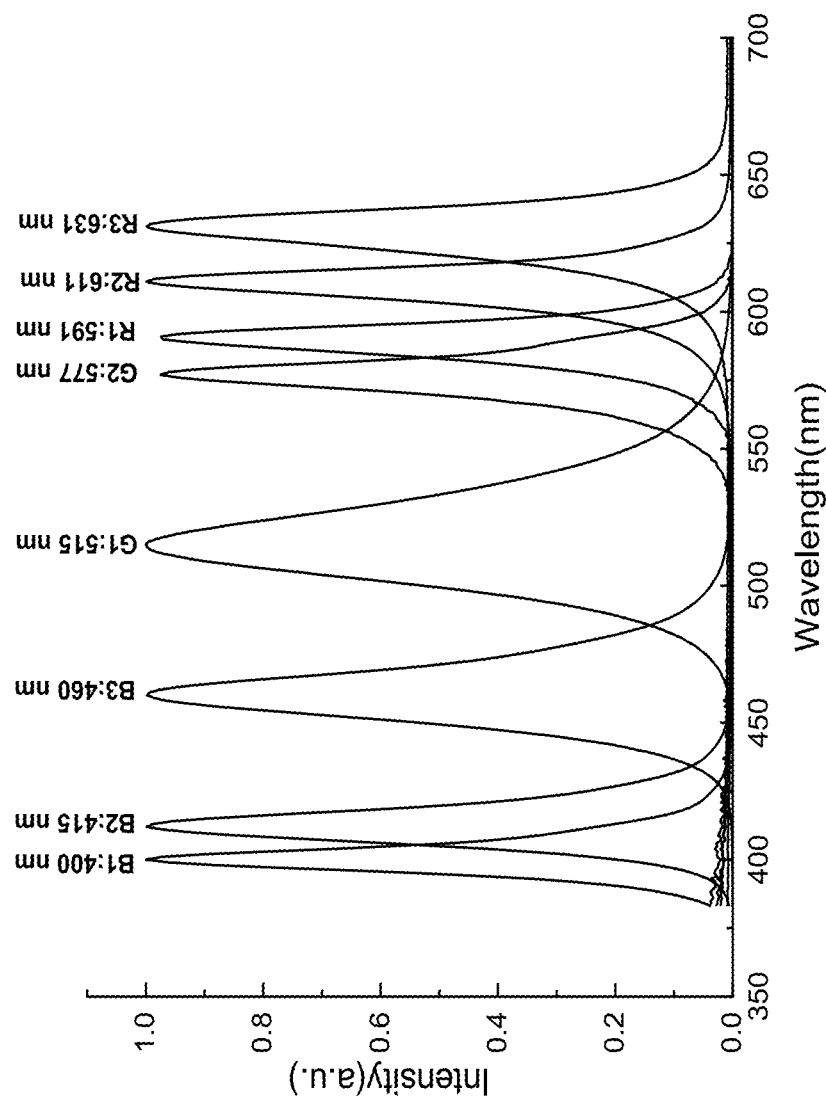
FIG. 3A is a graph of the intensity of a plurality of wavelength subranges corresponding to a plurality of different respective color groups of LEDs, according to some embodiments of the invention.

High color quality in vivo imaging may be achieved by simulating a white light spectrum via the combination of different LED color groups. A white light illumination spectrum that simulates sunlight at 1.5 atmospheres is referred to as "AM1.5" (as shown in FIG. 3C). Embodiments of the invention may simulate an illumination spectrum of AM1.5 (or other solar or synthetic spectra, such as, "White LED" or "Fluorescent lamp" in FIG. 3C) using a combination of a plurality of colors from a plurality of color groups.

Each LED may produce one or more illumination spectra in an individual color group. For example, as shown in FIG. 3A, a red spectrum may comprise the color groups R1, R2, and/or R3. These color groups are represented by gaussian intensity profiles with maximums at 631 nm, 611 nm, and 591 nm, respectively. A blue spectrum may comprise the color groups B1, B2, and/or B3. These color groups are represented by gaussian intensity profiles with maximums at 400 nm, 415 nm, and 460 nm, respectively. A green spectrum may comprise the color groups G1 and/or G2. These color groups are represented by gaussian intensity profiles with maximums at 515 nm and 577 nm, respectively. For example, to simulate AM1.5 white light, some embodiments of the invention may activate one or more combinations of color groups (e.g., R1, G1, B1; R1, R2, G1, B1; or R1, R2, R3, G1, G2, B1, B2, B3).

Some embodiments of the invention may omit or reduce activation of a color group (e.g., only activating or biasing towards activating a subset of color groups) to simulate multi-color (non-white) light illumination. A color group may be omitted and/or reduced in intensity that has poor absorption for certain anatomical regions, to optimize illumination efficiency. An example where the omission of a color group may prove useful is Narrow Band Imaging (NBI). NBI is an endoscopic diagnostic procedure that omits or reduces red light and uses green and blue LEDs disproportionately to illuminate dense areas of superficial blood vessels. NBI takes advantage of the fact that hemoglobin poorly absorbs red light and has absorption peaks that favor green and blue light (e.g., as shown in FIG. 6D). In various embodiments of the invention, these multi-color light illumination spectra may be produced by activating any combination of a plurality of color groups (e.g., higher R1 illumination relatively to G1 and B1; R1, R2, R3, G1, B1; G1, G2, B1; R1, G1, B1, B2, B3; R1, R2, R1, G2, B1, B2; G1, G2, B1, B2; B1, B2, B3; G1, G2; R1, R2, R3).

Embodiments of the invention may illuminate in a non-visible wavelength range, for example, infrared (IR), ultraviolet (UV), radio and/or other non-visible or combination of visible and non-visible wavelengths. For IR spectra, or spectra comprising a combination of IR and other color groups, longer wavelengths typically penetrate deeper into biological tissue, than relatively shorter wavelengths. This discrepancy between penetration depths associated with light of various wavelengths provides a depth profile of the imaged tissue. This depth profile can be used to simulate a three-dimensional image of the biological tissue. In various embodiments of the invention, IR illumination spectra may be produced and optimized through any combination of a plurality of IR color groups (e.g., near-IR1, mid-IR1, far-IR1; e.g., near-IR1, near-IR2, near-IR3), any combination of a plurality of IR color groups and/or any other color group(s) from the same and/or different respective color groups (e.g. near-IR1, near-IR2, Radio, R1, R2; near-IR1, G1, mid-IR1, B3, far-IR1, far-IR2).

Embodiments of the invention may match the output illumination spectrum emitted by one or more color groups of LEDs to an optimal input imaging spectrum of one or more corresponding color filters of an image sensor to achieve a maximal or above threshold quantum efficiency (QE). An image sensor (e.g., 110 as shown in FIGS. 1A and/or 5A) may be a photoelectric sensor, such as a complementary metal oxide semiconductor (CMOS) image sensor, which comprises a photoelectric grid made up of (e.g., millions) of pixels. In order to produce color images, a color filter array, such as a Bayer filter, may be installed in front of the image sensor. This color filter array comprises multiple color filters (e.g., one for each pixel) that each allow certain wavelength ranges of light within a permitted spectrum (e.g., red, green, or blue) to pass to each individual pixel (e.g., with above threshold QE), and blocks or reduces the remaining wavelengths of light outside of that spectrum from reaching the individual pixel (e.g., allowing light to pass with a below threshold QE) (e.g., as shown in the QE graph of FIG. 5B). The image sensor may also be paired with miniature charge amplifiers (e.g., one for each pixel). When a photon strikes the pixel, the charge amplifier converts a corresponding photoelectric current to an output voltage. Matching the illumination spectrum of the LEDs to the sensor input imaging spectrum reduces wasted photons outside of the sensor's permitted imaging spectrum that would otherwise not be detected (or be detected with a corresponding QE that is below threshold). Illuminating at those optimal wavelengths increases the proportion of LED light to which the sensor pixels are exposed that contribute to its photoelectric current, referred to as the "quantum efficiency" (QE), as compared to illuminating with light at the same intensity outside of those optimal wavelength ranges. Embodiments of the invention may activate LEDs in any combination of color groups to achieve an illumination spectrum of the LEDs that matches or falls within the sensor input imaging spectrum, thereby increasing sensor exposure and improving the quantum efficiency of the system.

Figure 7A:
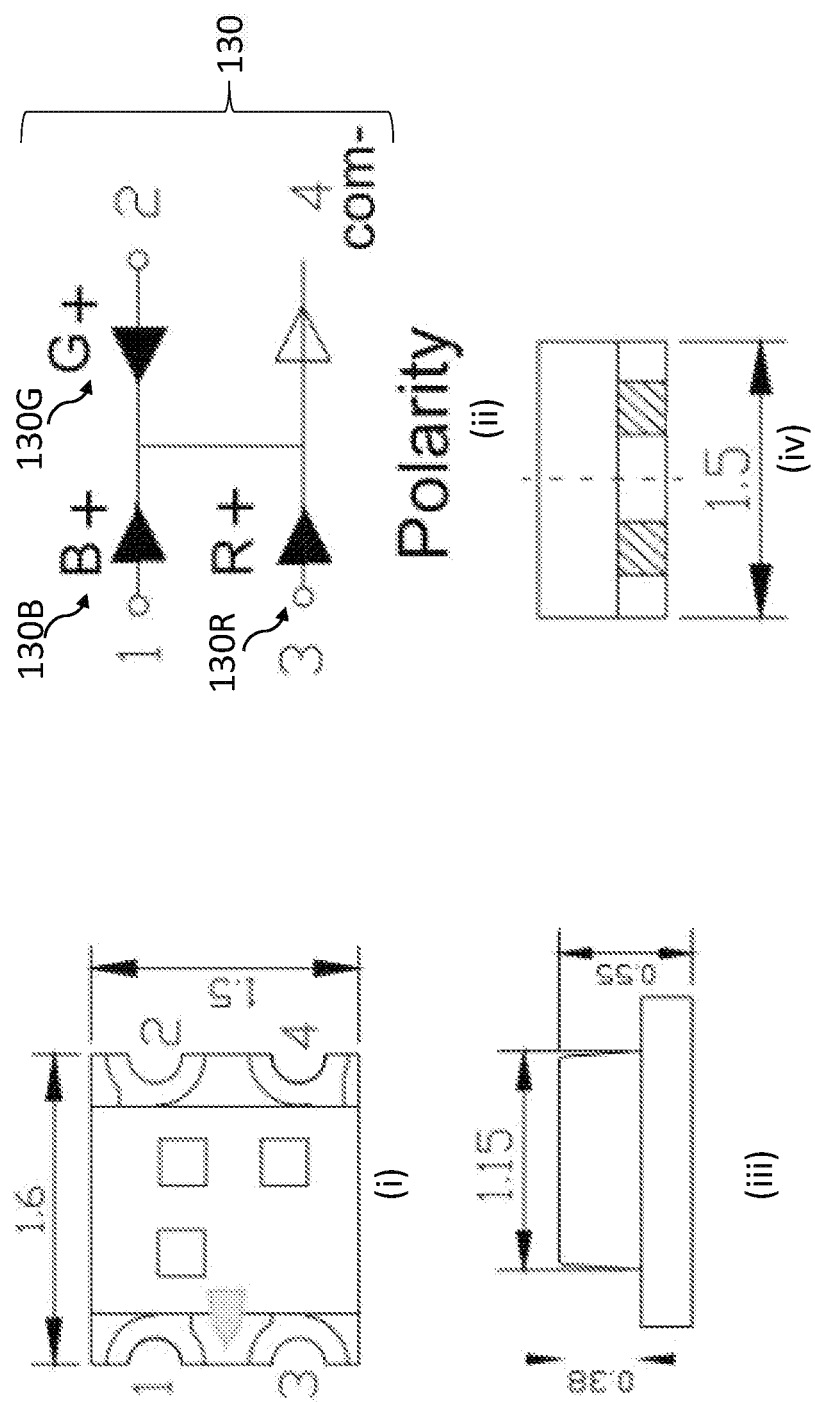
FIG. 7A is a schematic illustration of (i) a top view of an example circuit board for attaching LEDs, (ii) an example circuit diagram of LEDs attached to the example circuit board, and (iii) and (iv) side views of the example circuit board, according to some embodiments of the invention.

Reference is made to FIG. 1A, which schematically illustrates an exploded view of an in-vivo capsule endoscope 100 and components thereof, for illuminating the GI tract with a dynamic adjustable color illumination spectrum, according to an embodiment of the invention. In-vivo capsule endoscope 100 may be housed internal to capsule-shaped body 104. Capsule-shaped body 104 may have two concave shells or hemispheres at opposite ends of its longitudinal axis. Capsule endoscope 100 may have a one-sided or two-sided imaging system, such that, capsule-shaped body 104 may have at least one transparent optical end or shell 108 at one and/or both ends of its longitudinal axis, respectively. Capsule-shaped body 104 may enclose electronic components therein. Each transparent shell 108 may house one or more lens(es) 112 and LED array(s) 102. An image sensor(s) 110 configured to record in-vivo images may be housed interior to capsule-shaped body 104 behind the at least one transparent optical shell 108. LED array 102 may include a plurality of LEDs 130 mounted onto a circuit board. Example circuit diagrams of an LED circuit board and LEDs 130 are shown in FIG. 7A (i) and (ii), respectively. Lens 112 may comprise one or more lens(es) for focusing light emitted by LEDs 130 onto image sensor 110. Image sensor 110 may comprise one or more color filter array(s) (e.g., as shown in FIG. 5A). Image sensor 110 and/or image processing board 128 may include one or more processing circuit board(s) for executing operations (e.g., processing, storing, and/or sending image data) according to embodiments of the invention. Image sensor 110 and/or image processing board 128 may include one or more memories for storing data (e.g., color-specific, multi-color, or white light images) according to embodiments of the invention.

LED array 102 may comprise a plurality of different color groups of LEDs 130 configured to emit light to be recorded and/or stored by the image sensor 110, image processing board 128, and/or an external device processor operating in an external memory. The plurality of different color groups of LEDs 130 may correspond to a plurality of respective wavelength subranges, such that the LEDs 130 in each color group emit light in an illumination spectrum that falls within the color group's corresponding wavelength subrange. LED array 102 may also include, or is operably connected to, a driving circuit configured to adjust the combination, order, and/or durations of the time pulses and/or the power or driving currents of the LEDs 130. The driving circuit may, in turn, be coupled to an illumination processor (e.g., in image sensor 110 and/or image processing board 128) that controls its operation. The driving circuit may be configured to send a driving current to independently activate each different color group of LEDs 130 during distinct (e.g., entirely or partially non-overlapping) time pulses, such that, a single color group of LEDs is independently activated at any one time. The plurality of different color groups of LEDs 130 may be sequentially activated in successive time pulses to cumulatively simulate a white light or multi-color illumination spectrum over a plurality of time pulses. Image sensor 110 may be configured to sequentially record a plurality of different color groups of images depicting the scattering of light emitted from the respective plurality of different color groups of LEDs 130 during the entirely or partially non-overlapping time pulses. In some embodiments, the illumination processor may activate color groups of LEDs that substantially match the input optimal imaging spectrum of the color filter(s) of the image sensor 110 to increase or maximize the capsule's quantum efficiency.

Figure 1B:
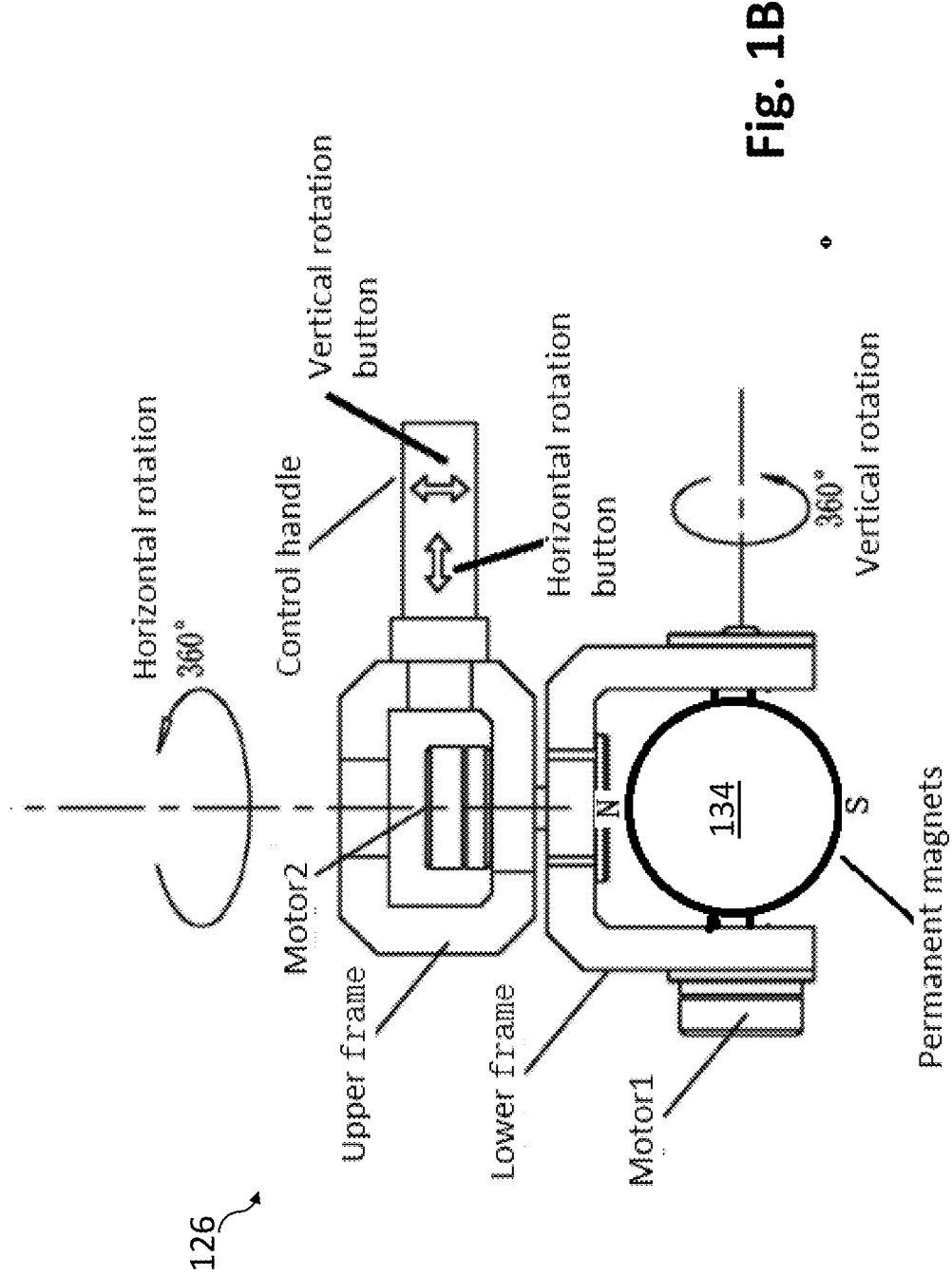
FIG. 1B is a schematic illustration of an external magnetic control system for moving the in-vivo capsule endoscope of FIG. 1A inside the GI tract, according to some embodiments of the invention.

In various embodiments, capsule endoscope 100 may be propelled through the GI tract magnetically (e.g., by the external magnetic control system as shown in FIG. 1B), or by peristalsis (non-magnetically). In embodiments using magnetic propulsion, capsule-shaped body 104 may also house one or more permanent magnet(s) 124 having a permanent magnetic dipole (e.g., North-South). Permanent magnets 124 allow capsule endoscope 100 to be magnetically guided when exposed to a magnetic field generated by an external magnetic control system as shown in FIG. 1B. Capsule-shaped body 104 may also house a wireless communication system 122 comprising a wireless (e.g., radio frequency (RF)) processing board and an antenna for wirelessly transmitting and receiving information to/from a remote device or controller. Capsule-shaped body 104 may also house one or more batteries or a power supply 132 to power the endoscope 100 components.

Wireless communication system 122 may transmit in-vivo information, such as, in-vivo image data captured by sensing device 110, location information (e.g., anatomical location, geographical location), magnetic field information for interacting with and being controlled by an external magnet control system, and/or other sensory feedback, e.g., in-vivo conditions such as temperature, pressure, pH, etc. Wireless communication system 122 may receive from a remote device or external controller commands or control information, such as, illumination activation patterns or commands and/or parameters. Wireless communication system 122 may transmit to and/or receive from a remote device or external controller, images and/or image quality or position information, such that optimization parameters of the driving circuit of the LED array 102 may be determined and implemented by a feedback loop that may trigger real-time adjustments in LED activation based on environmental conditions. The feedback loop may be executed locally in the capsule 100 (e.g., on the image processing board 128) and/or externally on a remote device or controller. In the case of local execution of the feedback loop on the image processing board 128, images and/or image quality information may be received directly by the image processing board 128 where optimal parameters of the driving circuit(s) of LED array 102 may be determined locally.

Reference is made to FIG. 1B, which schematically illustrates an external magnetic control system 126 for moving in-vivo capsule endoscope 100 inside the GI tract, according to embodiments of the invention. External magnetic control system 126 may generate a magnetic field to guide capsule endoscope 100 via one or more permanent magnet(s) 124 contained in capsule endoscope 100. External magnetic control system 126 includes fixtures adapted for horizontal and vertical positioning of one or more external permanent magnet(s) 134 by the use of vertically and horizontally adjustable mechanisms and an adjustable base. External magnetic control system 126 has freedom of movement along two axes to move capsule endoscope 100 in three dimensions. Details of the mechanics and operation of external magnetic control system 126 may be described, for example, in U.S. Patent Application Publication No. 2015/0380140, the entirety of which is hereby incorporated by reference.

Figure 2A:
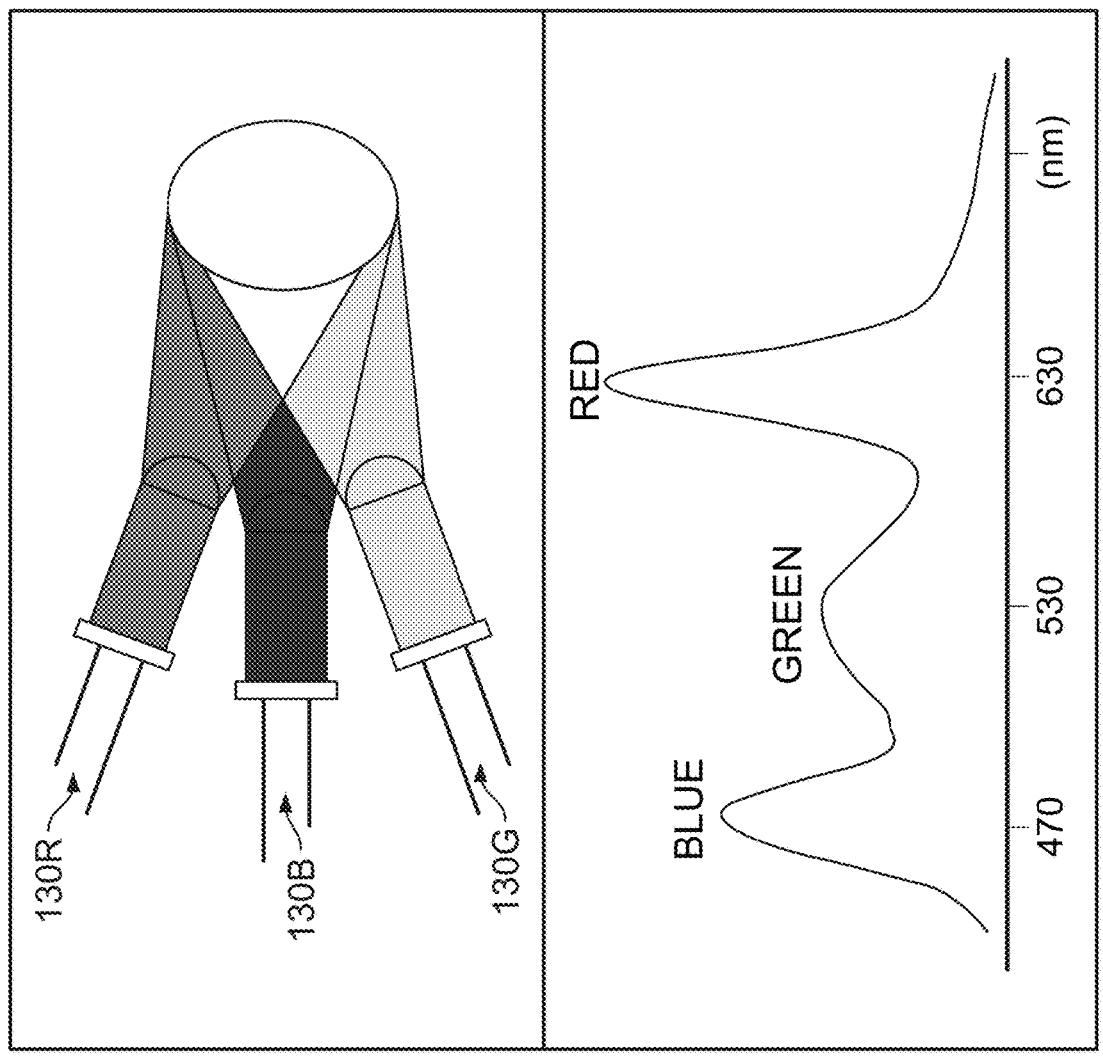
FIG. 2A is a schematic illustration of multiple color groups of LEDs for producing white light illumination, and their respective illumination spectra, according to some embodiments of the invention.

Reference is made to FIG. 2A, which schematically illustrates multiple colors groups of LEDs (130R, 130B, 130G) for producing white light illumination, and their respective illumination spectra, according to some embodiments of the invention. In some embodiments, any combination of color groups of LEDs and their respective time pulse widths and/or driving currents may be configured to produce this white light illumination spectrum. In some embodiments, any combination of color groups of LEDs and their respective time pulse widths and/or driving currents may be configured to produce a modified and/or optimized version of this white light illumination spectrum.

Figure 2B:
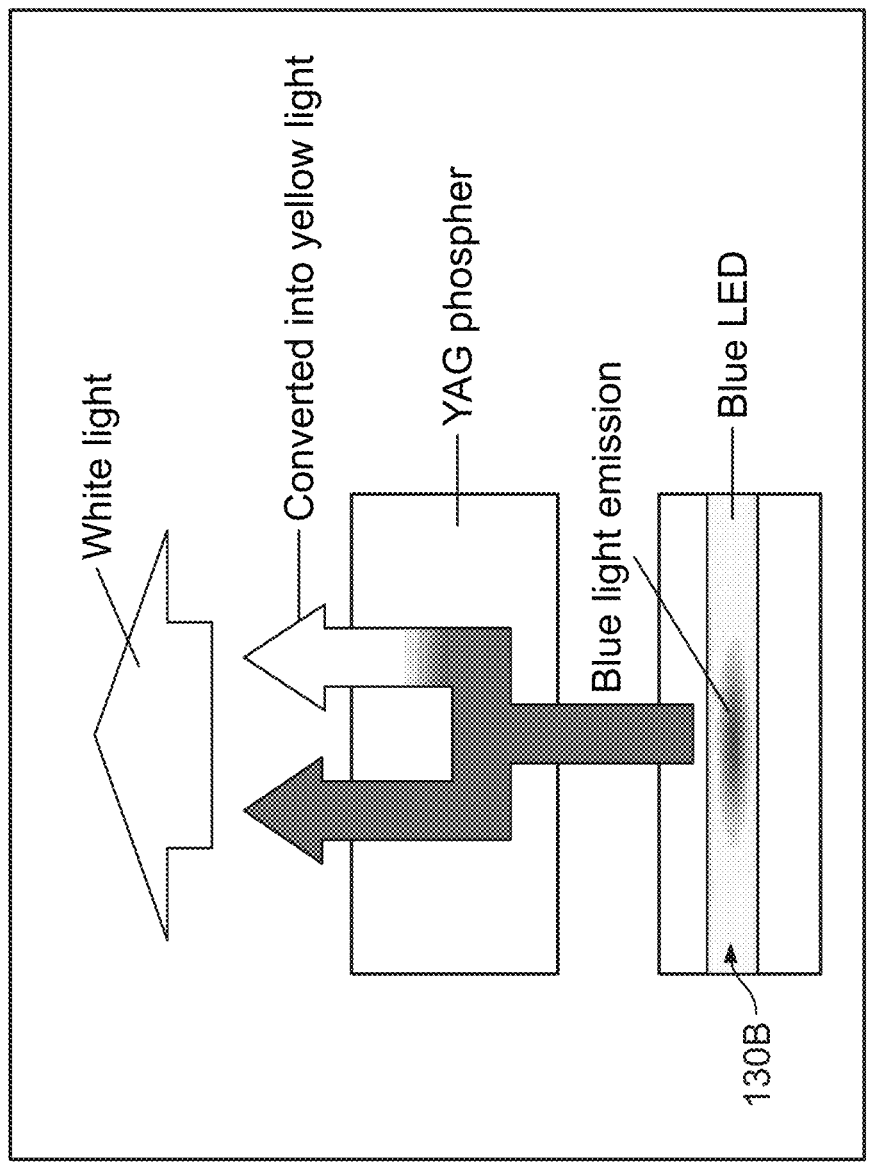
FIG. 2B is a schematic illustration of an LED in a single color group, split into multiple color groups by a filter, according to some embodiments of the invention.

Reference is made to FIG. 2B which schematically illustrates an LED in a single color group (e.g., blue), split into multiple color groups (e.g., blue and yellow) by a filter (e.g., a phosphor filter), according to some embodiments of the invention. Light from the multiple split color groups combines to form white light illumination. In some embodiments, the filter may be applied to LED array 102 to transform a single color input spectra to produce white light illumination.

Reference is made to FIG. 3A, which graphically displays the intensity of a plurality of wavelength subranges corresponding to a plurality of different respective color groups of LEDs, according to some embodiments of the invention. In some embodiments, any combination of these color groups of LEDs and their respective time pulse widths and/or driving currents may be configured to produce and optimize white light illumination or multi-colored (non-white) light illumination.

Figure 3B:
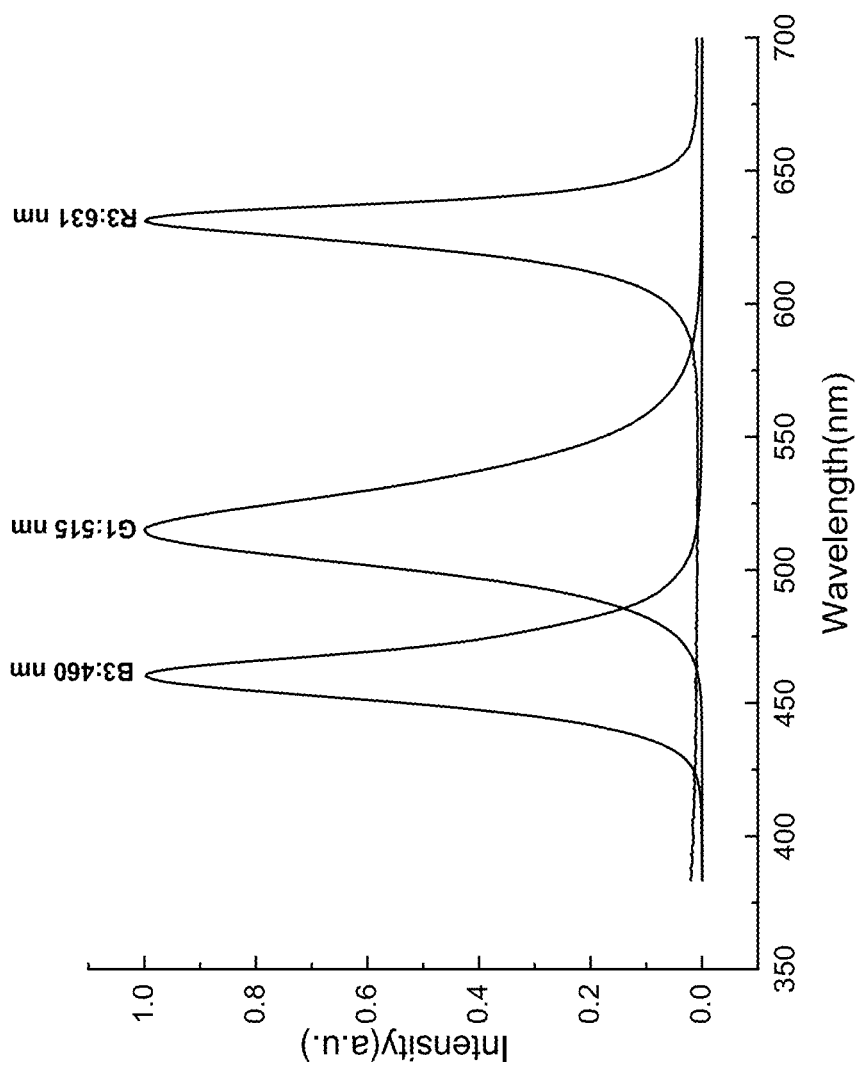
FIG. 3B is a graph of an illumination spectrum of the intensity of three example wavelength subranges corresponding to three different respective color groups of LEDs from FIG. 3A, according to some embodiments of the invention.
Figure 3C:
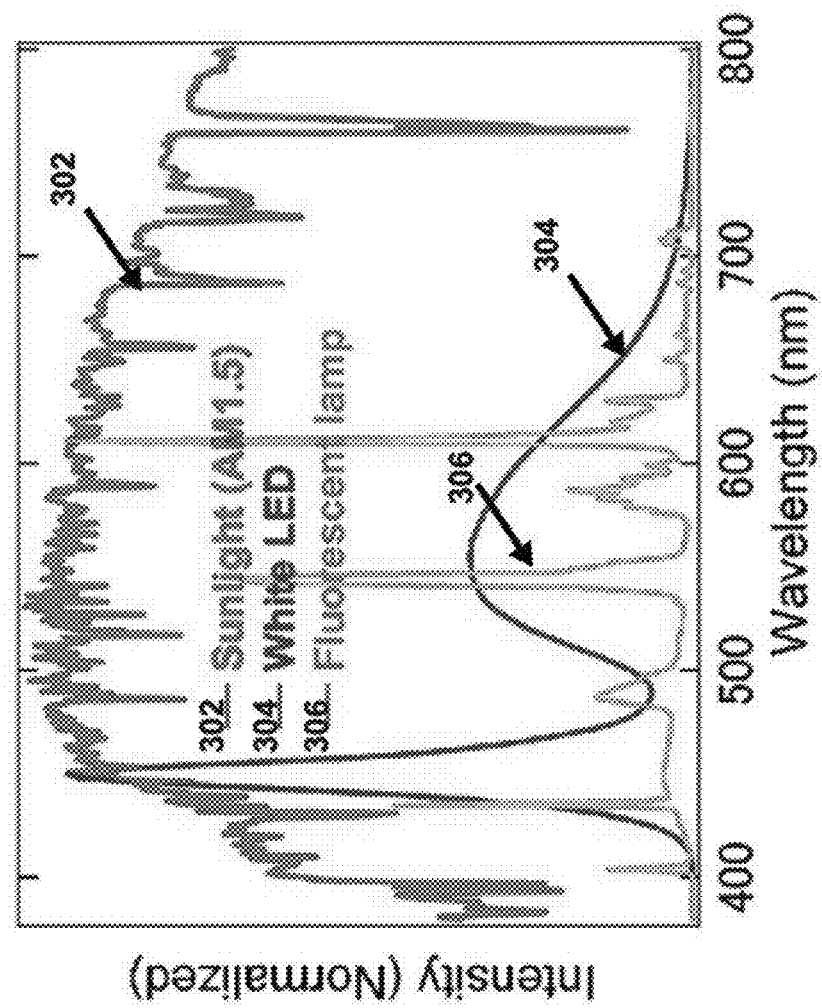
FIG. 3C is a graph of an illumination spectrum of the intensity of wavelength ranges of sunlight (e.g., AM1.5), an example LED white light, and an example fluorescent light, according to some embodiments of the invention.

Reference is made to FIG. 3B, which graphically displays an illumination spectrum of the intensity of three example wavelength subranges corresponding to three different respective color groups of LEDs from FIG. 3A, according to some embodiments of the invention. In some embodiments, any combination of these color groups of LEDs and their respective time pulse widths and/or driving currents may be configured to produce and optimize white light illumination or multi-colored (non-white) light illumination.

Reference is made to FIG. 3C, which graphically displays an illumination spectrum of the intensity of wavelength ranges of sunlight 302 (e.g. AM1.5), an example LED white light 304, and an example fluorescent light 306, according to some embodiments of the invention. In some embodiments, any combination of color groups of LEDs and their respective time pulse widths and/or driving currents may be configured to produce and optimize white light illumination such that its illumination spectrum simulates that of sunlight 302 (including AM1.5) or fluorescent light.

Reference is made to FIG. 4A, which schematically illustrates a close-up view of LED array 102, according to some embodiments of the invention. In some embodiments, a plurality of sets of LEDs 130 may be installed on the front face of LED array 102. Each set of LEDs 130 may comprise one or a plurality of different respective color groups of LEDs (e.g., 130R, 130G, and/or 130B). In some embodiments, the plurality of different color groups of LEDs 130 may be arranged in one or more clusters, where each cluster comprises LEDs from a plurality of different color groups (e.g., 130R 130B 130G). In some embodiments, a plurality of dedicated driving circuits may be installed on the back face of LED array 102. Each driving circuit may comprise a plurality of dedicated control circuits (e.g., as shown in FIG. 7C) configured to send a drive current to independently activate different respective color groups of LEDs by generating current pulses of various time pulse widths and/or various currents, according to some embodiments of the invention.

References is made to FIGS. 4B-4D which graphically illustrates a plurality of patterns of time pulses during which a plurality of different color groups of LEDs are independently activated, according to some embodiments of the invention. te (or a multiple thereof) represents the exposure time during which the imaging sensor captures an image. tb, tg, tr, and tir represent the illumination time pulses during which the blue, green, red and infrared color groups of LEDs are respectively activated. In some embodiments, any combination of color groups of LEDs and their respective time pulse widths and/or driving currents may be configured to produce and optimize white light illumination or multi-colored (non-white) light illumination. Although the intensity of the various color groups (height of illumination blocks) are constant in FIGS. 4B-4D, both the time pulses (widths) and intensities (heights) of the various color groups of LEDs may be independently and differently activated.

Reference is made to FIG. 5A, which schematically illustrates image sensor 110 with an example color pattern created by a color filter array, such as a Bayer filter, according to some embodiments of the invention. The color filter array comprises multiple color filters (e.g., one for each pixel) which allows each pixel to absorb light of a single wavelength range associated with a single color group. For example, a Bayer filter allows the wavelength subranges associated with three different respective color groups (e.g., red, green, blue) shown in FIG. 3B. Laterally adjacent pixels (e.g., horizontally and/or vertically, but not diagonally) absorb light of a different wavelength subrange associated with a different respective color group. Image sensor 110 may be configured such that incident light is split by the filter(s) into a plurality of color panels 110R(1), 110G(1), and 110B(1), each of which comprises a different single color groups, according to some embodiments of the invention. Light passing through each color group panel 110R(1), 110G(1), or 110B(1) forms a single color group image 110R(2), 110G(2), and 110B(2), respectively. In some embodiments of the invention, the output illumination spectrum emitted by each color group of LEDs may match or substantially overlap an optimal input spectrum (e.g., having high quantum efficiency) of a corresponding color group of the color filter array of the image sensor 110.

Figure 5B:
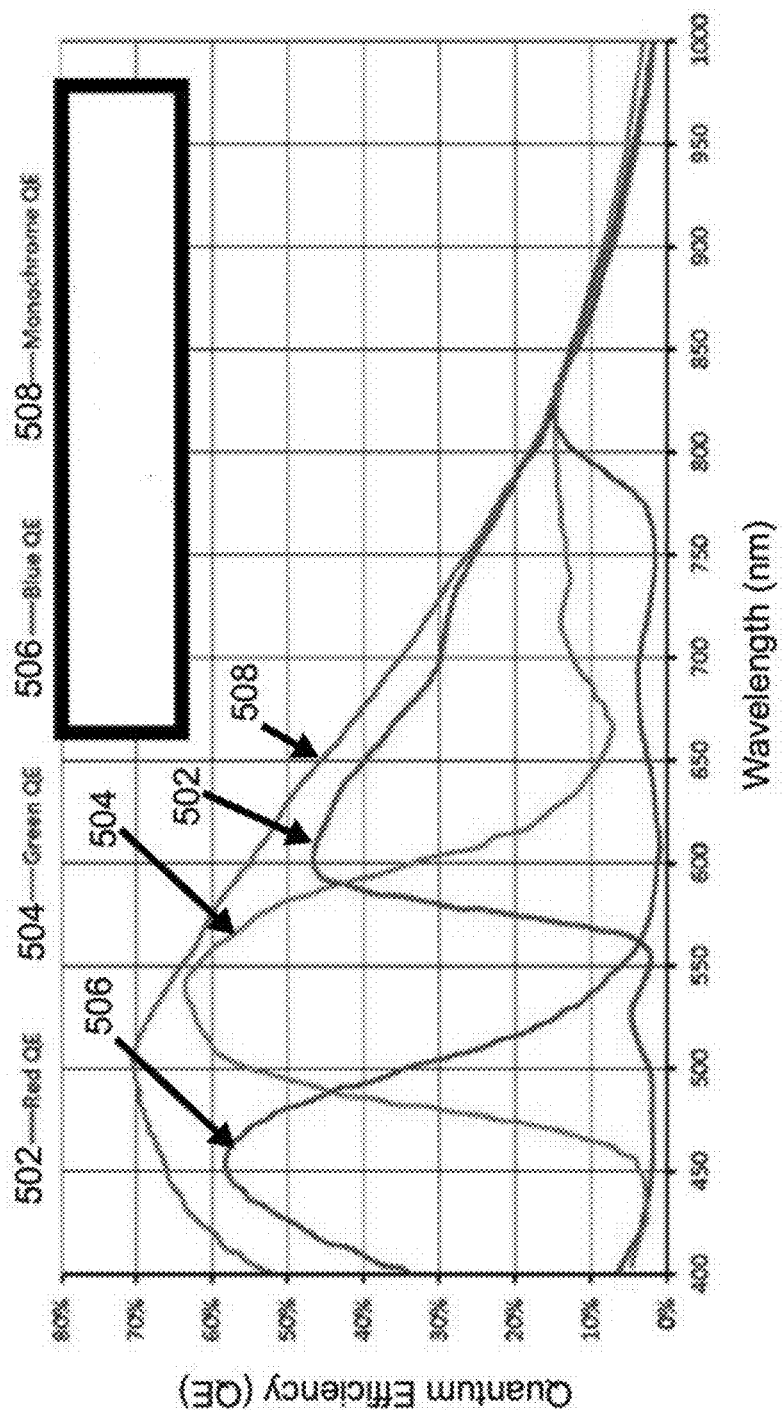
FIG. 5B is a graph of the Quantum Efficiency (QE) of an image sensor over a range of illumination wavelengths, according to some embodiments of the invention.

Reference is made to FIG. 5B, which graphically displays the Quantum Efficiency (QE) of an image sensor (e.g., 110 of FIG. 5A) over a range of illumination wavelengths, according to some embodiments of the invention. Curves 502, 504, and 506 show the quantum efficiency of the image sensor exposed to a color filter array of the three color groups red, green, and blue, respectively. Curve 508 shows the quantum efficiency of the image sensor exposed to light without an overlaid color filter array. The absence of a color filter array thus causes the image sensor to capture a monochrome or black and white image. Embodiments of the invention may match the output illumination spectrum emitted by each color group of LEDs to an optimal input imaging spectrum of a corresponding color filter array of the image sensor associated with a maximal or above threshold quantum efficiency (QE). In some embodiments of the invention, the time pulses and current strengths of the LEDs may be adjusted or tuned as variables to optimize the QE (e.g., to achieve a maximal or above threshold QE).

Figure 6A:
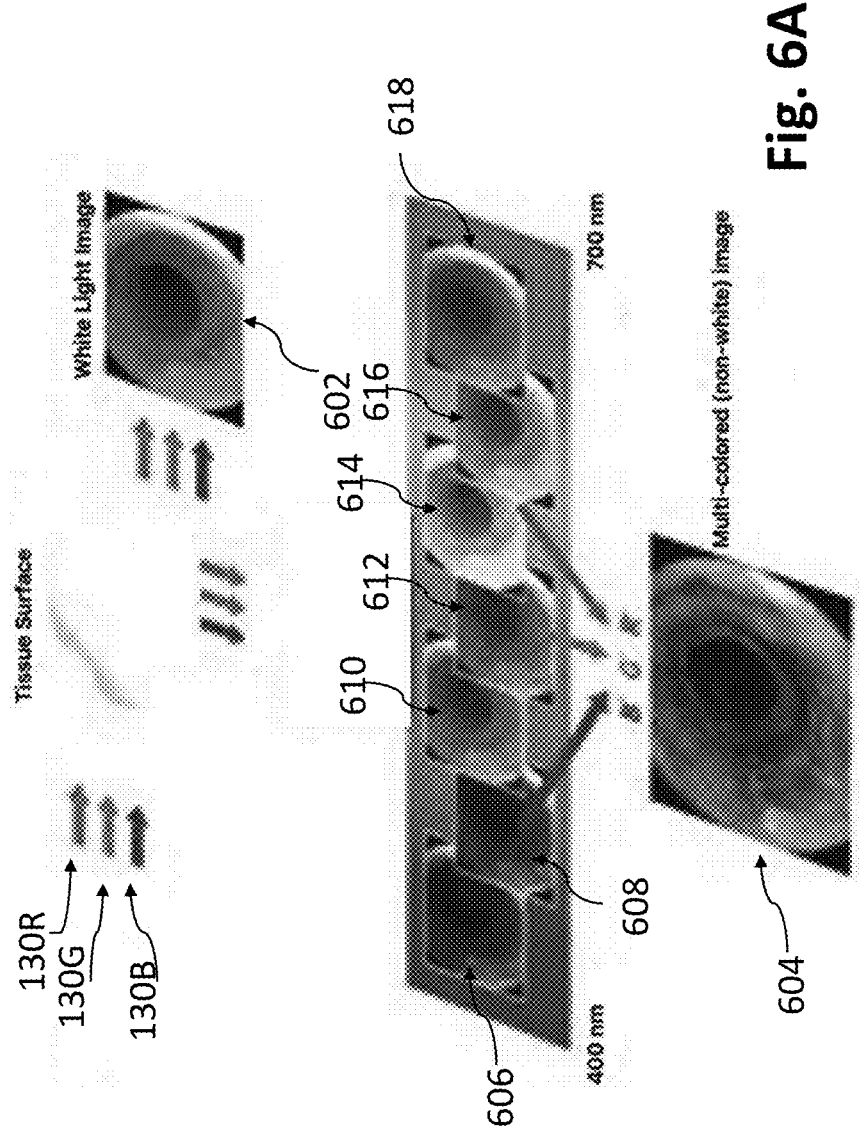
FIG. 6A is a schematic illustration a system for illuminating biological tissue to generate a white light image or a multi-color (non-white light) image, according to some embodiments of the invention.

Reference is made to FIG. 6A, which schematically illustrates a system for illuminating biological tissue to generate a white light image and/or a multi-color (non-white light) image, according to some embodiments of the invention. Biological tissue may be sequentially illuminated by different respective color groups of LEDs (e.g., 130R, 130G, 130B) and may scatter the respective color groups of LED illumination. The color groups of LED illumination may then be absorbed by an image sensor (e.g., 110 of FIG. 1A) to form respective color-group specific images 606-618. Color-group specific images 606-618 may either be combined to generate a white light image 602 and/or a multi-color (non-white) image 604. Multi-color (non-white) images 604 may be produced according to embodiments of this invention in a more efficient manner than flexible spectral imaging color enhancement (FICE). FICE is an endoscopic imaging technique in which biological tissue is illuminated by white light. This white light is scattered by the biological tissue and is recorded by an image sensor (e.g., color CCD) to form white light images. An adaptive filtering engine (i.e., FICE engine) then decomposes the white light image by specific wavelengths into multi-color (non-white) images, which is a complex and time-consuming process. Embodiments of the invention may generate multi-color (non-white) images 604 that are similar or equivalent to FICE images by using color-specific illumination instead of white light illumination, thereby avoiding the need to use an adaptive filtering engine to decompose color-specific images. Obviating the need for the time-consuming adaptive filtering color decomposition used in the FICE engine, allows embodiments of this invention to generate multi-color (non-white) images 604 faster and more efficiently than the FICE engine.

Figure 6B:
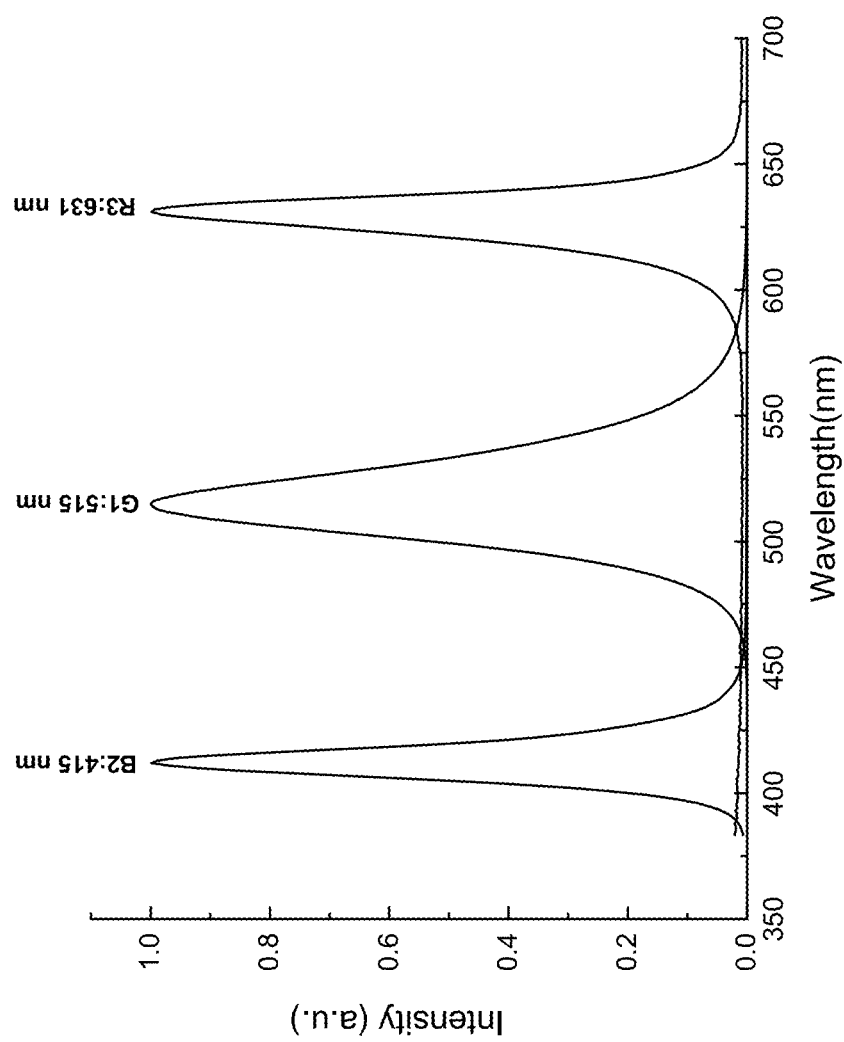
FIG. 6B is a graph of the intensity of three example wavelength subranges corresponding to three different respective color groups of LEDs that combine to produce the white light image of FIG. 6A, according to some embodiments of the invention.

Reference is made to FIG. 6B, which graphically displays three example wavelength subranges corresponding to three different respective color groups of LEDs that combine to produce the white light image in FIG. 6A, according to embodiments of the invention. In some embodiments, any combination of color groups of LEDs and their respective time pulse widths and/or driving currents may be configured to produce, optimize and/or modify a white light illumination spectrum.

Figure 6C:
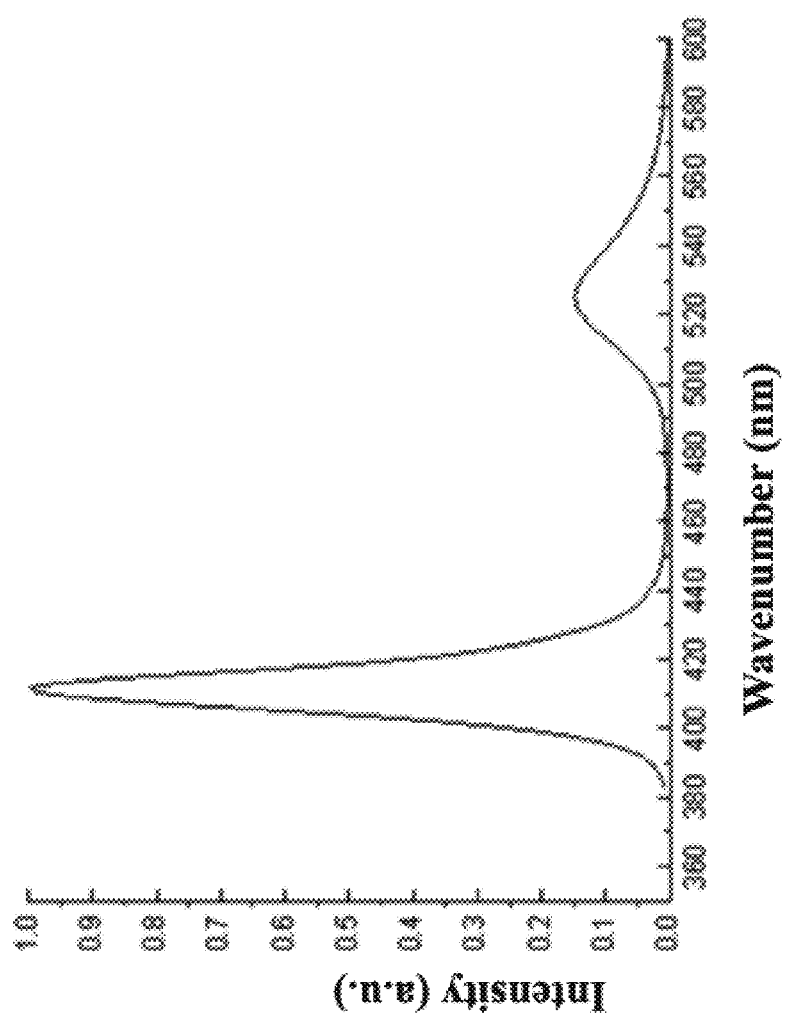
FIG. 6C is a graph of an illumination spectrum of the intensity of two example wavelength subranges corresponding to two different respective color groups of LEDs that combine to produce the multi-color (non-white light) image of FIG. 6A, according to some embodiments of the invention.
Figure 6D:
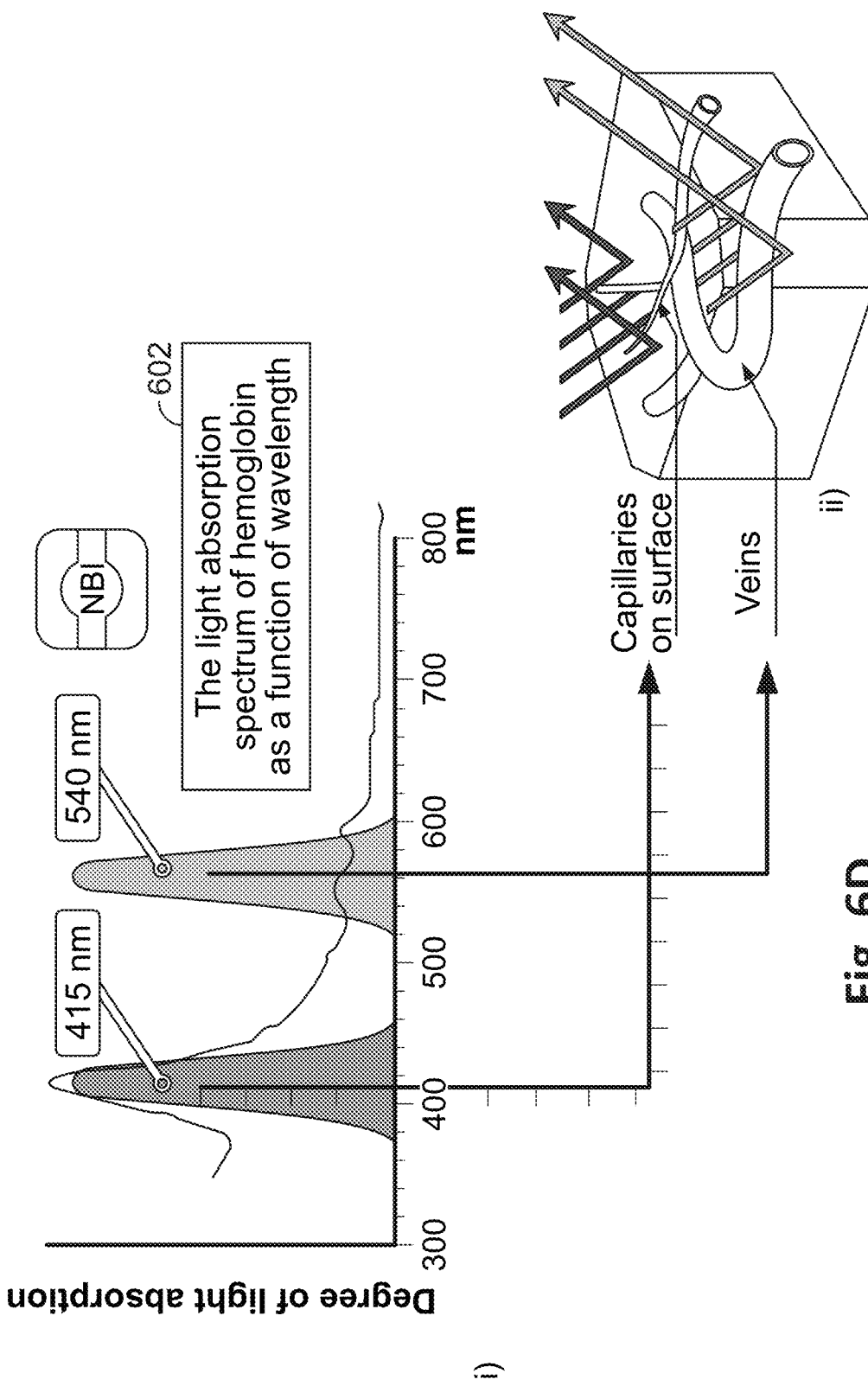
FIG. 6D is a schematic illustration of (ii) biological tissue penetrated at various depths by incident light in a plurality of different wavelength subranges corresponding to a plurality of different respective color groups of LEDs, and (i) a corresponding multi-colored (non-white) light absorption spectrum and respective wavelength subranges corresponding to a plurality of different respective color groups of LEDs, according to some embodiments of the invention.

Reference is made to FIG. 6C, which graphically displays an illumination spectrum of the intensity of two example wavelength subranges corresponding to two different respective color groups of LEDs that combine to produce the multi-color (non-white) light image in FIG. 6A, according to embodiments of the invention. In some embodiments, any combination of color groups of LEDs and their respective time pulse widths and/or driving currents may be configured to produce, optimize and/or modify a multi-colored (non-white) illumination spectrum.

Reference is made to FIG. 6D, which schematically illustrates (ii) biological tissue penetrated at various depths by incident light in a plurality of different wavelength subranges corresponding to a plurality of different respective color groups of LEDs, and (i) a corresponding multi-colored (non-white) light absorption spectrum and respective wavelength subranges corresponding to a plurality of different respective color groups of LEDs, according to some embodiments of the invention. In the example of FIG. 6D, a multi-colored (non-white) illumination spectrum of blue and green color groups causes a corresponding multi-colored (non-white) light absorption spectrum of blue and green color groups by the image sensor. Curve 602 in FIG. 6D (i) shows that hemoglobin has absorption bands predominantly at approximately 415 nm (corresponding to blue LED light) and 540 nm (corresponding to green LED light). Embodiments of the invention may take advantage of the color preference of hemoglobin by independently activating the preferred color groups of LEDs to emit a multi-colored (non-white) illumination spectrum comprising blue and green LED light. The illumination spectrum may be customized to the intensities and wavelength of a hemoglobin curve, e.g. 602, in order to better image blood-rich anatomical regions, such as, dense networks of superficial blood vessels near the tracheobronchial tree and the colorectal region.

FIG. 6D (ii) shows that green LED light has a greater penetrative depth into biological tissue than does blue LED light. In general, LED light with relatively longer wavelengths (shorter frequencies) will penetrate tissue at relatively greater depths, whereas LED light with relatively shorter wavelengths (higher frequencies) will penetrate tissue at relatively shallower depths. For example, relatively long wavelength IR LED light may be used to penetrate biological tissue at greater depths than visible light. The discrepancy between different penetrative depths may be used to generate a topological map or depth profile of the imaged biological tissue. Such a topological map or depth profile of the imaged biological tissue may be used to simulate a three-dimensional model of the biological tissue and build three-dimensional images of anatomical structures.

Reference is made to FIG. 7A, which schematically illustrates (i) a top view of an example circuit board for attaching LEDs, (ii) an example circuit diagram of LEDs 130 attached to the example circuit board, and (iii) and (iv) side views of the example circuit board, according to some embodiments of the invention. As shown in FIG. 7A (ii), cathode pins of LEDs 130R, 130G, 130B may be connected to a common pin (connection "4" in FIG. 7A (ii)) that the battery and/or power supply 132 supplies with a negative signal. Furthermore, the anode pins of LEDs 130R, 130G, 130B (connections 3, 2, 1 in FIG. 7A (ii) respectively) may be supplied a positive signal by the battery and/or power supply 132, according to some embodiments of the invention. In some embodiments, the LED cluster 130, as shown in FIG. 7A (ii), may be installed on to the front of the circuit board shown in FIG. 7A (i).

Figure 7B:
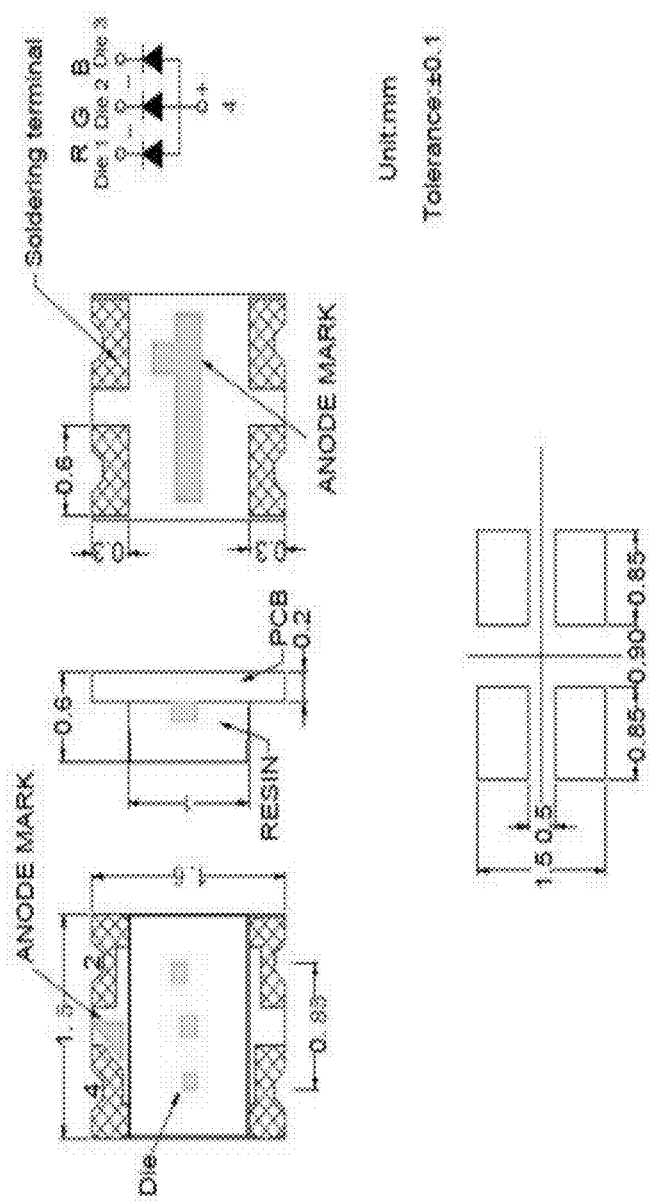
FIG. 7B is a schematic illustration of a structure and packaging which may house an LED circuit board, according to embodiments of the invention.

Reference is made to FIG. 7B, which schematically illustrates a structure and packaging which may house an LED circuit board, according to embodiments of the invention.

Reference is made to FIG. 7C, which schematically illustrates a driving circuit 700 comprising a plurality of dedicated control circuits (e.g., 700R, 700G, 700B), each of which independently activates a different respective color group of LEDs (e.g., 130R, 130G, 130B, respectively) by generating current pulses of various time pulse widths and/or various currents, according to some embodiments of the invention. The driving circuit 700 may be configured to adjust combination, order, and/or duration of the time pulses and/or driving currents of each color group of LEDs (e.g. 130R, 130G, 130B). The driving circuit 700 may be installed on the back face of a substrate holding an LED array (e.g., 102 of FIG. 1) and/or coupled to an illumination processor that controls its operation (e.g., mounted on image processing board 128 of FIG. 1).

Reference is made to FIG. 8, which is a table listing a plurality of different respective color groups of LEDs and their corresponding peak wavelengths, full width half maximums, and beam angles, according to some embodiments of the invention. These values are used for example only, and any other values or combination of these or other color groups and their respective peak wavelengths, full width half maximums, and beam angles, may be used.

Figure 9:
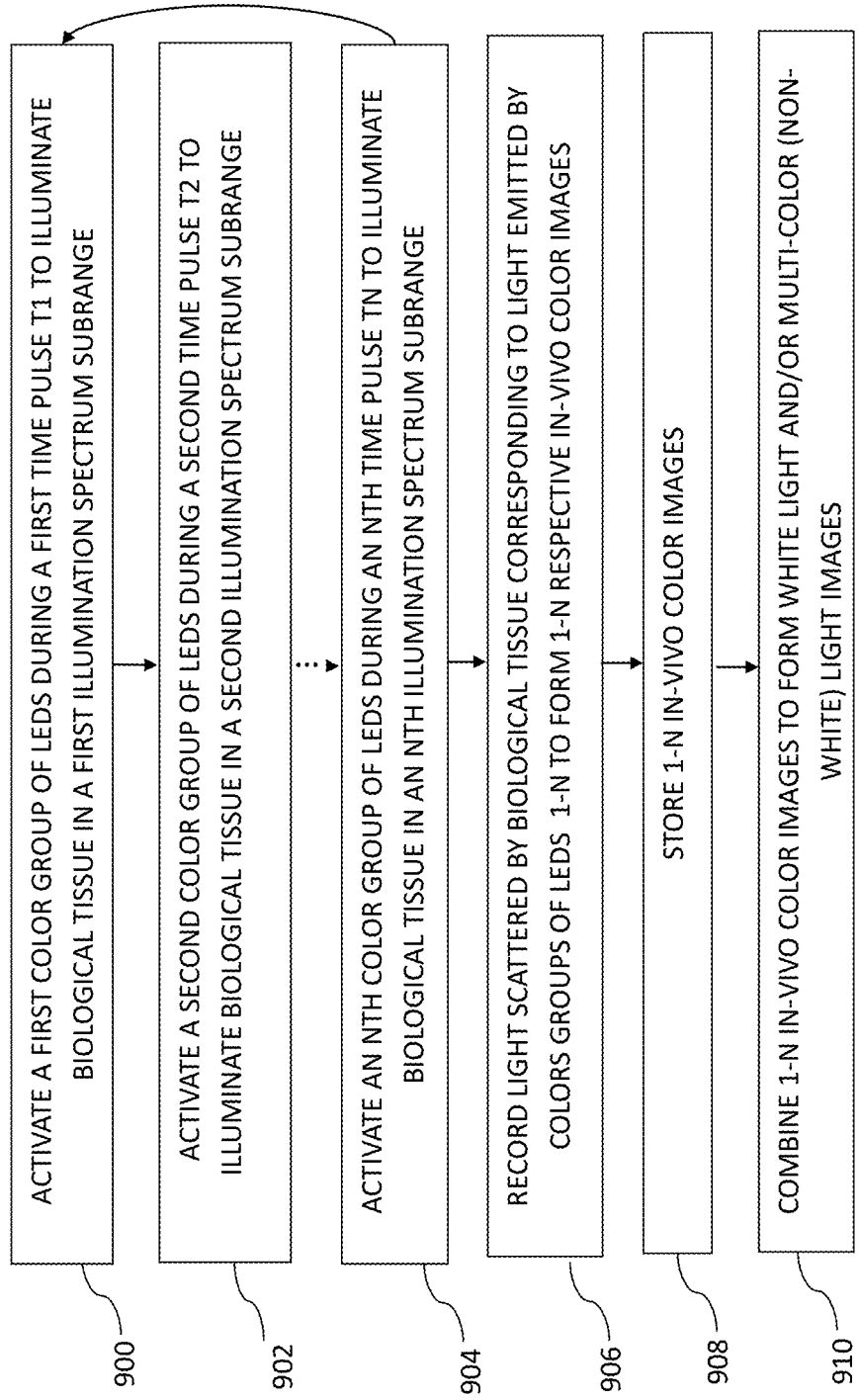
FIG. 9 is a flowchart of a method of operating an in-vivo capsule endoscope to emit a dynamic adjustable color illumination spectrum, according to some embodiments of the invention.

Reference is made to FIG. 9, which is a flowchart of a method for operating an in-vivo capsule endoscope to emit a dynamic adjustable color illumination spectrum, according to some embodiments of the invention. The operation(s) of FIG. 9 may be executed using devices or components of the capsule endoscope disclosed in reference to one or more of FIGS. 1-8. For example, one or more operations of FIG. 9 may be executed by one or more processors, using one or more memories, of an image sensor (e.g., 110 of FIGS. 1 and/or 5A), image processing board (e.g., 128 of FIG. 1A), and/or an external processor operating an external memory.

In operation 900, one or more processors (e.g., in image sensor 110 of FIGS. 1A and 5A, image processing board 128 of FIG. 1A, and/or an external processor), may activate a first color group of LEDs (e.g., 130R, 130B, or 130G of FIGS. 2A, 2B, 4A, and 6A) during a first time pulse T1. The one or more processors may control one or more control circuits (e.g., 700R, 700G, 700B of FIG. 7C), for example, where each distinct control circuit is dedicated to independently activating (e.g., via a driving current) a distinct one of the 1-N plurality of different color groups of LEDs. The first color group of LEDs may illuminate biological tissue with light in a unique wavelength subrange distinct (e.g., partially or entirely non-overlapping) from wavelength subranges of the other color groups.

In operation 902, the one or more processors may activate a second color group of LEDs (e.g., 130R, 130B, or 130G of FIGS. 2A, 2B, 4A, and 6A) during a second time pulse T2 distinct from other time pulses (e.g., T1, T3, . . . ). The second color group of LEDs may illuminate biological tissue with light in a unique wavelength subrange relative to the other color groups. After activating the second color group, the process or processor may proceed to sequentially activate each ith color group of LEDs during an ith time pulse Ti from i=3, . . . , N−1, and may proceed to operation 904 when i=N.

In operation 904, the one or more processors may activate an Nth color group of LEDs (e.g., 130R, 130B, or 130G of FIGS. 2A, 2B, 4A, and 6A) during an Nth time pulse TN. The one or more processors may sequentially activate the 1-N plurality of different color groups of LEDs during entirely or partially non-overlapping time pulses T1-TN. The 1-N plurality of different color groups of LEDs may illuminate biological tissue with light in a plurality of different respective wavelength subranges, such that the LEDs in each color group emit light in a unique illumination spectrum subrange for that color group that is different relative to the spectrum subrange for all other color groups. After activating one complete cycle of all 1-N LED color groups in T1-TN time pulses, the process or processor may return to operation 900 to repeat the illumination pattern, or adjust the illumination pattern for example as follows.

In some embodiments, the one or more processors may dynamically adjust activation of LED color groups, e.g., by dynamically adjusting their activation durations Ti of the T1-TN entirely or partially non-overlapping time pulses and/or intensities of driving circuit currents for activating one or more of the 1-N plurality of different color groups of LEDs, thereby adjusting the proportion with which the 1-N different color groups of images are activated and combined. Adjusting the proportion of illumination by various color group combinations dynamically adjusts the overall cumulative color illumination spectrum (e.g., of the resulting white light or non-white multi-color images combined in operation 910). In some embodiments, the one or more processors may dynamically adjust activation of LED color groups (e.g., via adjusting the duration Ti of the T1-TN entirely or partially non-overlapping time pulses and/or the intensity of the driving currents) in response to a feedback loop. The feedback loop may be based on image or position information collected by the capsule endoscope e.g., in real-time. For example, a feedback loop indicating the capsule is located in the stomach or is capturing images with a certain absorption spectrum may cause the one or more processors to adjust the activation of the LED color groups to be optimized to stomach lighting or optimal light for that certain absorption spectrum.

In some embodiments, the one or more processors may illuminate the biological tissue at different penetrative depths by light emitted from the different respective 1-N plurality of color groups of LEDs (e.g., as shown in FIG. 6D). The one or more processors may then generate a depth profile of the biological tissue based on the discrepancy between the penetration depths. The one or more processors may then simulate a three-dimensional image of the biological tissue based on the depth profile.

In operation 906, one or more processors (e.g., in image sensor 110 of FIGS. 1A and 5A, image processing board 128 of FIG. 1A, and/or an external processor) may sequentially record a 1-N plurality of different color groups of images depicting the scattering of light emitted from the respective 1-N plurality of color groups of LEDs during the entirely or partially non-overlapping T1-TN time pulses. In some embodiments, the one or more processors may select a pattern of LED color group activation, such that the illumination spectrum of the combination of the activated color groups (e.g., combining to form white light or non-white multi-color images) matches an absorption spectrum of the image sensor. In some embodiments, the one or more processors may match the illumination spectrum emitted by one or more color group of LEDs to an optimal absorption spectrum of the image sensor e.g., associated with a maximal or above threshold quantum efficiency (QE).

In some embodiments, the one or more processors may record color group-specific images, such that, each image depicts a single color group and is recorded during activation of a single color group of LEDs, and no other color group of LEDs. Additionally or alternatively, the one or more processors may record mixed color group images, such that, each image depicts multiple color groups and is recorded over multiple time pulses when multiple color group of LEDs are activated. In some embodiments, when mixed color group images are recorded by an image sensor, a process or processor may skip or reduce the instances of operation 910 for combining color-specific images.

In operation 908, one or more processors (e.g., in image sensor 110 of FIGS. 1A and 5A, image processing board 128 of FIG. 1A, and/or an external processor) may store the 1-N plurality of different color groups of images recorded in operation 906.

In operation 910, one or more processors (e.g., image sensor 110 of FIGS. 1A and 5A, image processing board 128 of FIG. 1A, and/or an external processor) may combine color group-specific images from two or more different color groups to form white light or non-white multi-color images. In some embodiments, the one or more processors may combine the entirety and/or subsets of the 1-N plurality of different color groups of images to form white light and/or multi-color (non-white) light images.

Other or additional operations may be executed in the same or different order.

In some embodiments, color may refer not only to electromagnetic (EM) waves in the visible spectrum, but also to EM waves in the non-visible spectrum, such as, in the infrared (IR) or ultraviolet (UV) color group.

Embodiments of the invention may include an article such as a non-transitory computer or processor readable medium, or a computer or processor non-transitory storage medium, such as for example a memory, a disk drive, or a USB flash memory, encoding, including or storing instructions, e.g., computer-executable instructions, which, when executed by a processor or controller (e.g., in image sensor 110 of FIGS. 1A and 5A, image processing board 128 of FIG. 1A, and/or an external processor), carry out methods disclosed herein.

In the above description, an embodiment is an example or implementation of the inventions. The various appearances of "one embodiment," "an embodiment" or "some embodiments" do not necessarily all refer to the same embodiments. Although various features of the invention may be described in the context of a single embodiment, the features of embodiments may also be provided separately or in any suitable combination. Conversely, although the invention may be described herein in the context of separate embodiments for clarity, the invention may also be implemented in a single embodiment. Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions. It will further be recognized that the aspects of the invention described hereinabove may be combined or otherwise coexist in embodiments of the invention.

The descriptions, examples, methods and materials presented in the claims and the specification are not to be construed as limiting but rather as illustrative only. While certain features of the present invention have been illustrated and described herein, many modifications, substitutions, changes, and equivalents may occur to those of ordinary skill in the art. It is, therefore, to be understood that the appended claims are intended to cover all such modifications and changes as fall with the true spirit of the invention.

While the invention has been described with respect to a limited number of embodiments, these should not be construed as limitations on the scope of the invention, but rather as exemplifications of some of the preferred embodiments. Other possible variations, modifications, and applications are also within the scope of the invention. Different embodiments are disclosed herein. Features of certain embodiments may be combined with features of other embodiments; thus certain embodiments may be combinations of features of multiple embodiments. Accordingly, the scope of the invention should not be limited by what has thus far been described, but by the appended claims and their legal equivalents.

The invention claimed is:

1. A capsule endoscope with a dynamic adjustable color illumination spectrum, the capsule endoscope comprising:
   a capsule-shaped body having at least one transparent optical end, the capsule-shaped body enclosing electronic components therein;
   an image sensor housed interior to the capsule-shaped body behind the at least one transparent optical end, the image sensor configured to record in-vivo images;
   a first group of light emitting diodes (LEDs) each having a single first color, second group of LEDs each having a single second color, and third group of LEDs having a single third color, each group configured to emit light to be recorded by the image sensor, the first, second, and third group of single color LEDs corresponding to a plurality of different respective wavelength subranges, wherein the first color, the second color and the third color are different; and
   a driving circuit configured to send a driving current to independently activate each of the first, second, and third group of single color LEDs during entirely non-overlapping time pulses that occur sequentially, such that, one of the first, second, or third single color group of LEDs is independently activated at any one time to simulate a white light or multi-color illumination spectrum over a plurality of time pulses,
   wherein different color groups of LEDs emit light absorbed by biological tissue at different respective penetrative depths, such that the discrepancy between the penetration depths generates a depth profile of the illuminated biological tissue, and comprising one or more processors configured to simulate an image of the biological tissue based on the depth profile.

2. The capsule endoscope of claim 1, wherein the driving circuit is configured to dynamically adjust a duration of the entirely non-overlapping time pulses or an intensity of a driving current for activating one or more of the first group, second group, and third group of LEDs.

3. The capsule endoscope of claim 2, wherein the driving circuit is configured to dynamically adjust the duration of the entirely non-overlapping time pulses or the intensity of the driving current in response to a feedback loop based on image or position information collected by the capsule endoscope in real-time.

4. The capsule endoscope of claim 1, wherein the driving circuit is coupled to a plurality of dedicated control circuits, each of the plurality of dedicated control circuits is configured to respectively independently activate a different one of the first, second, and third group of single color LEDs.

5. The capsule endoscope of claim 1, wherein the image sensor is configured to record each image of a single color group when a single color group of LEDs, and no other color group of LEDs, is activated.

6. The capsule endoscope of claim 1 comprising one or more processors configured to combine images from two or more of a first, second, and third group of single color groups of images to form white light or non-white multi-color images.

7. The capsule endoscope of claim 1, wherein the image sensor is configured to record a white light or non-white multi-color image depicting the scattering of light emitted from two or more of the first group, the second group, and the third group of LEDs during two or more respective time pulses.

8. The capsule endoscope of claim 1, comprising one or more processors configured to activate one or more of the first group, the second group, and the third group of LEDs that emit light in wavelength subranges that match an absorption spectrum of the image sensor.

9. The capsule endoscope of claim 1, wherein the plurality of color groups of LEDs are arranged in one or more clusters, each cluster comprising LEDs from two or more of the first group, the second group, and the third group of LEDs.

10. A method of operating an in-vivo capsule endoscope to emit a dynamic adjustable color illumination spectrum, the method comprising:
    sequentially activating a first group of light emitting diodes (LEDs) each having a single first color, second group of LEDs each having a single second color, and third group of LEDs having a single third color, each group during respective, first, second and third entirely non-overlapping time pulses that occur sequentially, wherein the first group, the second group, and the third group of LEDs illuminate biological tissue with light in a plurality of different respective wavelength subranges;
    sequentially recording, at an image sensor, a first, second, and third group of images depicting the scattering of light emitted from the respective first group, the second group, and the third group of LEDs during the entirely non-overlapping time pulses as archived images;
    storing the plurality of different color groups of images; and
    selecting and adjusting the archived images to form white light or non-white multi-color images.

11. The method of claim 10 comprising dynamically adjusting a duration of the entirely non-overlapping time pulses or an intensity of a driving current for activating one or more of the first group, the second group, and the third group of LEDs to adjust a proportion with which the different color groups of images are combined for adjusting an illumination spectrum of the white light or non-white multi-color images.

12. The method of claim 11 comprising dynamically adjusting the duration of the entirely non-overlapping time pulses or the intensity of the driving current in response to a feedback loop based on image or position information collected by the capsule endoscope in real-time.

13. The method of claim 10 comprising activating each of the first group, the second group, and the third group of LEDs independently by a different color group dedicated control circuit.

14. The method of claim 10 comprising recording each image of a single color group when a single color group of LEDs, and no other color group of LEDs, is activated.

15. The method of claim 10, wherein the white light or non-white multi-color images are combined from two or more of the plurality of different color group images recorded during a plurality of entirely non-overlapping time pulses when the first, second, and third group of single color LEDs are activated.

16. The method of claim 10 comprising matching an illumination spectrum of the white light or non-white multi-color images to an absorption spectrum of the image sensor.

17. The method of claim 10 comprising:
illuminating the biological tissue at different penetrative depths by light emitted from the different respective the first group, the second group, and the third group of LEDs;
generating a depth profile of the biological tissue based on the discrepancy between the penetration depths; and
simulating a three-dimensional image of the biological tissue based on the depth profile.

* * * * *